US012730069B2

(12) United States Patent
Howard

(10) Patent No.: US 12,730,069 B2
(45) **Date of Patent: *Sep. 8, 2026**

(54) CARTRIDGE-BASED AUTOMATED RAPID TEST ANALYZER

(71) Applicant: Genesis Intelligence, LLC, Jacksonville, FL (US)

(72) Inventor: Newton Howard, Washington, DC (US)

(73) Assignee: Genesis Intelligence, LLC, Jacksonville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/704,467

(22) Filed: Mar. 25, 2022

(65) Prior Publication Data

US 2022/0214277 A1 Jul. 7, 2022

Related U.S. Application Data

(63) Continuation-in-part of application No. 16/855,709, filed on Apr. 22, 2020.

(60) Provisional application No. 63/280,783, filed on Nov. 18, 2021, provisional application No. 62/988,320, filed on Mar. 11, 2020, provisional application No. 62/991,906, filed on Mar. 19, 2020, provisional application No. 62/993,222, filed on Mar. 23, 2020, provisional application No. 62/994,165, filed on Mar. 24, 2020, provisional application No. 63/001,291, filed on Mar. 28, 2020.

(51) Int. Cl.

| | |
|---|---|
| ***G01N 21/64*** | (2006.01) |
| ***B01L 3/00*** | (2006.01) |
| ***G01N 15/1433*** | (2024.01) |
| ***G01N 33/533*** | (2006.01) |
| ***G01N 33/543*** | (2006.01) |
| ***G01N 33/569*** | (2006.01) |
| *G01N 15/075* | (2024.01) |
| *G01N 21/77* | (2006.01) |

(52) U.S. Cl.

CPC .... *G01N 21/6428* (2013.01); *B01L 3/502715* (2013.01); *G01N 15/1433* (2024.01); *G01N 33/533* (2013.01); *G01N 33/54333* (2013.01); *G01N 33/56983* (2013.01); *B01L 2200/16* (2013.01); *G01N 15/075* (2024.01); *G01N 2021/6439* (2013.01); *G01N 2021/7786* (2013.01); *G01N 2469/10* (2013.01); *G01N 2469/20* (2013.01)

(58) Field of Classification Search

None

See application file for complete search history.

(56) References Cited

U.S. PATENT DOCUMENTS

| | | | | |
|---|---|---|---|---|
| 6,649,128 | B1 * | 11/2003 | Meyer | G01N 35/028 422/50 |
| 2006/0134713 | A1 * | 6/2006 | Rylatt | G01N 33/543 435/7.92 |
| 2006/0148096 | A1 * | 7/2006 | Jina | G01N 33/723 436/514 |
| 2010/0248258 | A1 * | 9/2010 | Lee | B01F 33/30 435/7.1 |
| 2017/0284922 | A1 * | 10/2017 | Mermod | C12M 47/04 |
| 2019/0344269 | A1 * | 11/2019 | Johnson | B01L 3/502738 |

FOREIGN PATENT DOCUMENTS

| | | | |
|---|---|---|---|
| WO | WO 99/35486 | * 7/1999 | G01N 21/64 |
| WO | WO 2006138561 | * 12/2006 | C12Q 1/68 |
| WO | WO 2015150742 | * 10/2015 | |

* cited by examiner

*Primary Examiner* — Ann Montgomery

(74) *Attorney, Agent, or Firm* — Neo IP

(57) ABSTRACT

Embodiments may include a rapid test device that provide rapid detection of substances, including those involved in pathogen infection, for example, using Microscale Affinity Chromatography (MAC), indirect ELISA, and optical molecular sensing technology. For example, in an embodiment, a system may comprise a cartridge comprising a first chamber configured to receive a test sample including a target substance, the first chamber pre-filled with micromagnetic particles treated so as to bind to the target substance, and a first reservoir pre-filled with at least one reagent labeled with at least one fluorescent compound, the reagent adapted to bind to micromagnetic particles that are bound to the target substance, and an apparatus comprising a light source disposed so as to excite the least one fluorescent compound with a light and an optical sensor disposed so as to detect an emitted spectrum of light from the excited least one fluorescent compound.

8 Claims, 33 Drawing Sheets

(a)
(b)
(c)
202
204
206
208
210
212
214
216
Direct immobilization strategy
Protein A/G-mediated immobilization strategy
Secondary Ab-mediated immobilization strategy
Secondary Ab
Target Ab
Protein A/G
Antigen
Thiol group

400

402

406

408

Sample Loaded on Chip

408

412

410

408

410

404

Sample is loaded onto etched capillary columns

414

Virus attaches to antibodies, fluorophore simultaneously released

416

Concentrated sample is eluted for analysis

424

Optical Sensing "Box"

418

Light source

420

Wavelength analysis

422

Optical Sensing

Results sent to Phone

426

500

502

Sample Loaded on Chip

506

508

504

508

510

512

514

Mix magnetic particles/antigen with sample

508

516

518

520

Mix flour-escent compound with sample

522

524

526

Wash with buffer, move to detection

528

532

Light source

530

Wavelength analysis

534

Optical Sensing

536

Optical Sensing "Box"

Results sent to Phone

538

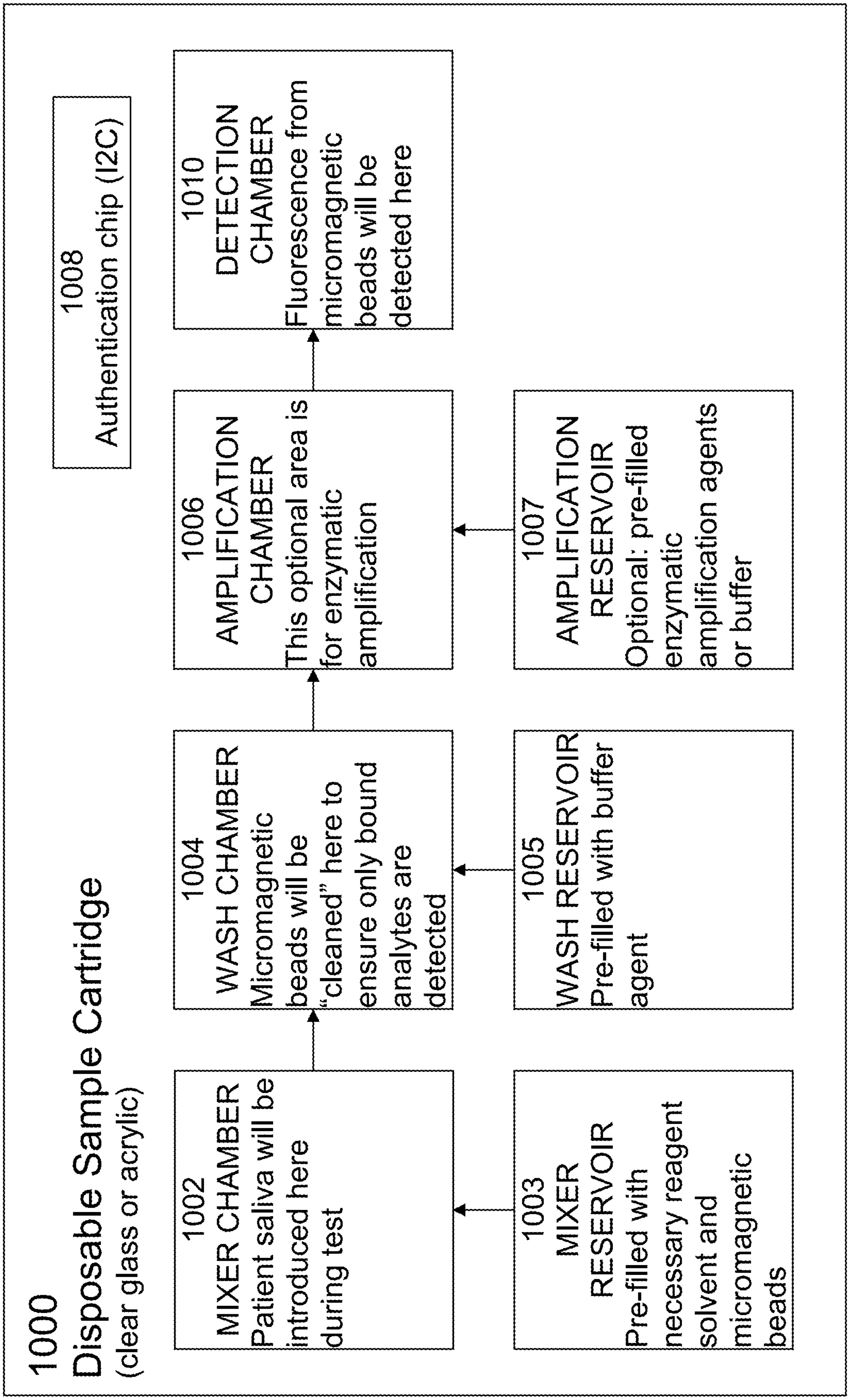

Fig. 10
1000
Disposable Sample Cartridge
(clear glass or acrylic)
1008
Authentication chip (I2C)
1002
MIXER CHAMBER
Patient saliva will be introduced here during test
1004
WASH CHAMBER
Micromagnetic beads will be "cleaned" here to ensure only bound analytes are detected
1006
AMPLIFICATION CHAMBER
This optional area is for enzymatic amplification
1010
DETECTION CHAMBER
Fluorescence from micromagnetic beads will be detected here
1003
MIXER RESERVOIR
Pre-filled with necessary reagent solvent and micromagnetic beads
1005
WASH RESERVOIR
Pre-filled with buffer agent
1007
AMPLIFICATION RESERVOIR
Optional: pre-filled enzymatic amplification agents or buffer 1102
Power
Supply
1104
LED Display
&
Membrane
Switch
1106
USB
1108
µController
1110
Servo Motor
Drivers
1112
Detection &
Authentication
1114
LED
Driver
1116
LEDs
500nm
1102
1122
Sample
Cartridge
1118
Servo Motor &
Magnet
1120
Multispectral
Photodiode
Chips
1100

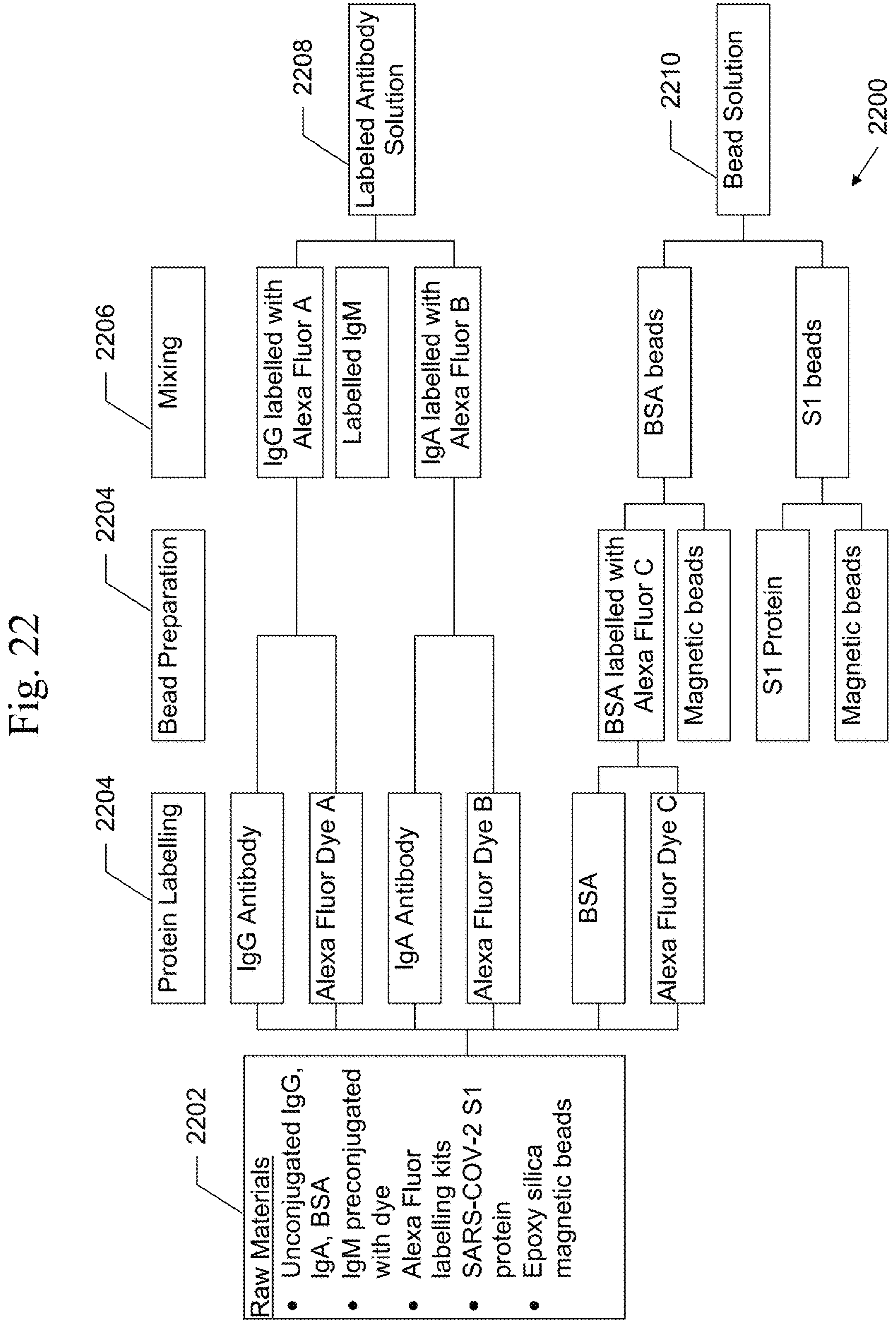
Fig. 22
2200
2202
Raw Materials
• Unconjugated IgG, IgA, BSA
• IgM preconjugated with dye
• Alexa Fluor labelling kits
• SARS-COV-2 S1 protein
• Epoxy silica magnetic beads
2204
Protein Labelling
IgG Antibody
Alexa Fluor Dye A
IgA Antibody
Alexa Fluor Dye B
BSA
Alexa Fluor Dye C
2204
Bead Preparation
BSA labelled with Alexa Fluor C
Magnetic beads
S1 Protein
Magnetic beads
2206
Mixing
IgG labelled with Alexa Fluor A
Labelled IgM
IgA labelled with Alexa Fluor B
BSA beads
S1 beads
2208
Labeled Antibody Solution
2210
Bead Solution

| 2800<br>Startup or Cartridge Switch Open |
|---|
| 2801<br>Display message e.g. “Preparing” |
| 2802<br>Perform motor position calibration |
| 2803<br>Display message e.g. “Ready” |

| 2810<br>On Lid Switch Open |
|---|
| 2811<br>If a test was in progress, abort. Display message e.g. “Test aborted”. The test can not be resumed because the cartridge is ruined. |
| 2812<br>Display message e.g. “Insert New Cartridge” |

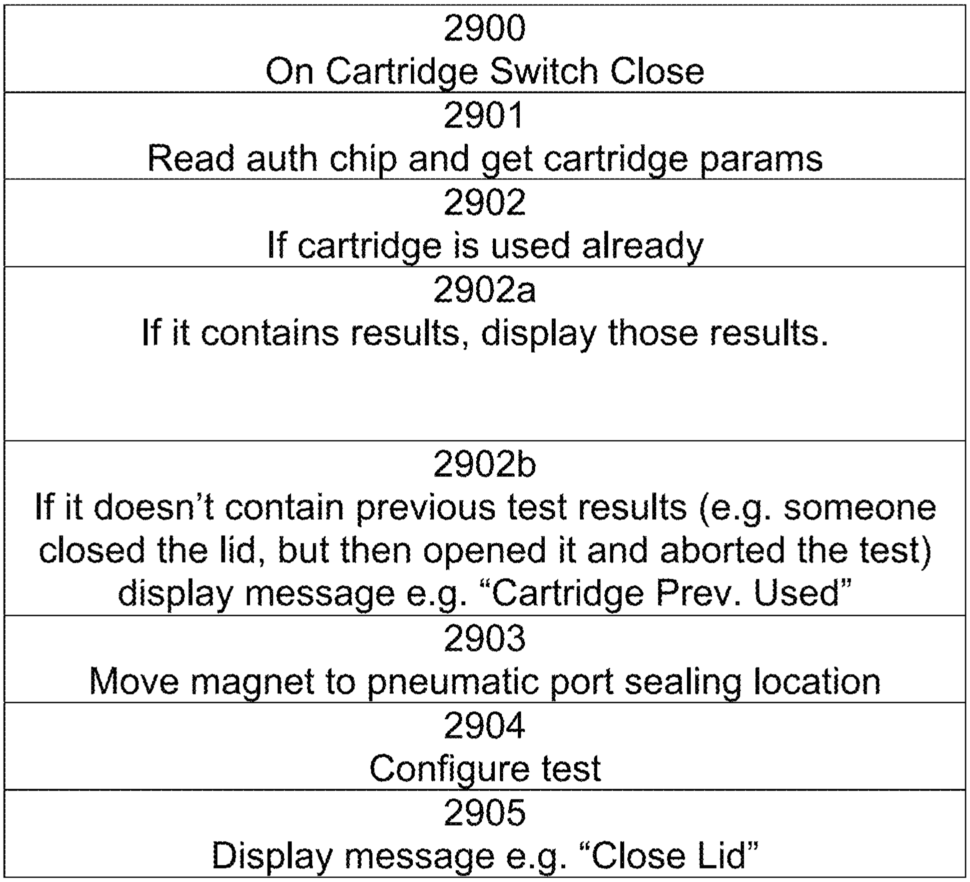

Fig. 29

| 2900<br>On Cartridge Switch Close |
|---|
| 2901<br>Read auth chip and get cartridge params |
| 2902<br>If cartridge is used already |
| 2902a<br>If it contains results, display those results. |
| 2902b<br>If it doesn't contain previous test results (e.g. someone closed the lid, but then opened it and aborted the test) display message e.g. "Cartridge Prev. Used" |
| 2903<br>Move magnet to pneumatic port sealing location |
| 2904<br>Configure test |
| 2905<br>Display message e.g. "Close Lid" |

Fig. 30a

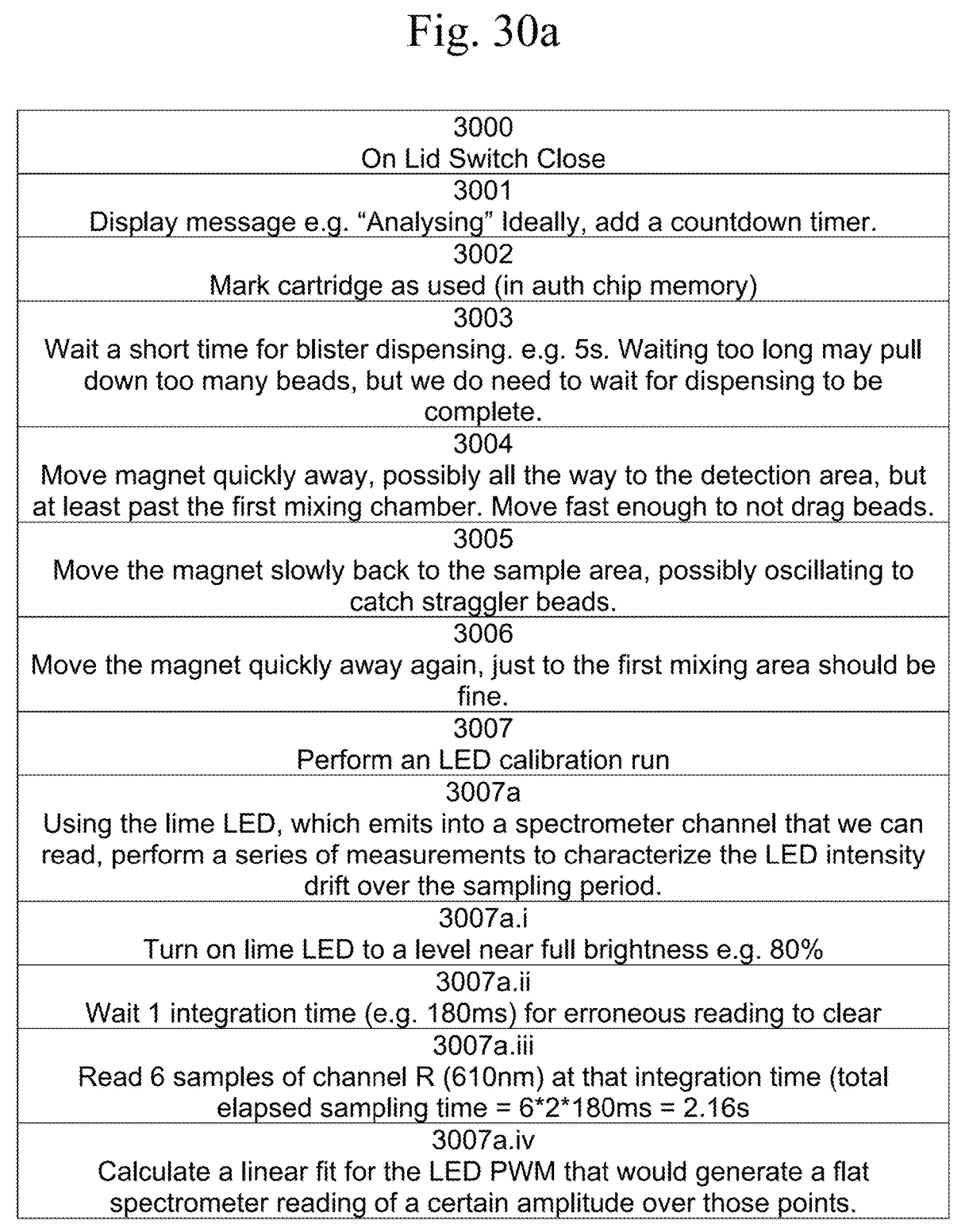

| |
|---|
| 3000<br>On Lid Switch Close |
| 3001<br>Display message e.g. “Analysing” Ideally, add a countdown timer. |
| 3002<br>Mark cartridge as used (in auth chip memory) |
| 3003<br>Wait a short time for blister dispensing. e.g. 5s. Waiting too long may pull down too many beads, but we do need to wait for dispensing to be complete. |
| 3004<br>Move magnet quickly away, possibly all the way to the detection area, but at least past the first mixing chamber. Move fast enough to not drag beads. |
| 3005<br>Move the magnet slowly back to the sample area, possibly oscillating to catch straggler beads. |
| 3006<br>Move the magnet quickly away again, just to the first mixing area should be fine. |
| 3007<br>Perform an LED calibration run |
| 3007a<br>Using the lime LED, which emits into a spectrometer channel that we can read, perform a series of measurements to characterize the LED intensity drift over the sampling period. |
| 3007a.i<br>Turn on lime LED to a level near full brightness e.g. 80% |
| 3007a.ii<br>Wait 1 integration time (e.g. 180ms) for erroneous reading to clear |
| 3007a.iii<br>Read 6 samples of channel R (610nm) at that integration time (total elapsed sampling time = 6*2*180ms = 2.16s |
| 3007a.iv<br>Calculate a linear fit for the LED PWM that would generate a flat spectrometer reading of a certain amplitude over those points. |

Fig. 30b

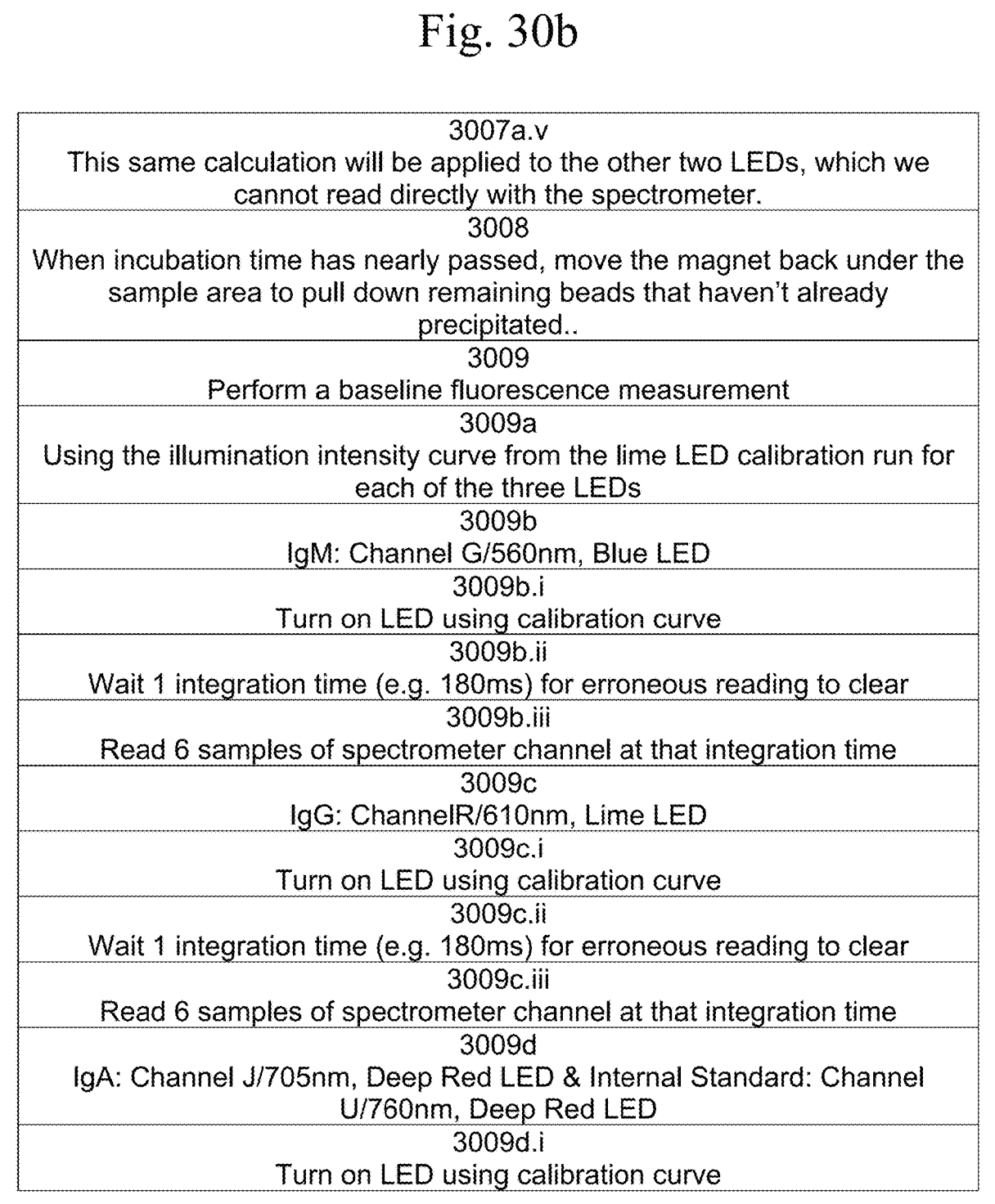

| |
|---|
| 3007a.v<br>This same calculation will be applied to the other two LEDs, which we cannot read directly with the spectrometer. |
| 3008<br>When incubation time has nearly passed, move the magnet back under the sample area to pull down remaining beads that haven't already precipitated.. |
| 3009<br>Perform a baseline fluorescence measurement |
| 3009a<br>Using the illumination intensity curve from the lime LED calibration run for each of the three LEDs |
| 3009b<br>IgM: Channel G/560nm, Blue LED |
| 3009b.i<br>Turn on LED using calibration curve |
| 3009b.ii<br>Wait 1 integration time (e.g. 180ms) for erroneous reading to clear |
| 3009b.iii<br>Read 6 samples of spectrometer channel at that integration time |
| 3009c<br>IgG: ChannelR/610nm, Lime LED |
| 3009c.i<br>Turn on LED using calibration curve |
| 3009c.ii<br>Wait 1 integration time (e.g. 180ms) for erroneous reading to clear |
| 3009c.iii<br>Read 6 samples of spectrometer channel at that integration time |
| 3009d<br>IgA: Channel J/705nm, Deep Red LED & Internal Standard: Channel U/760nm, Deep Red LED |
| 3009d.i<br>Turn on LED using calibration curve |

Fig. 30c

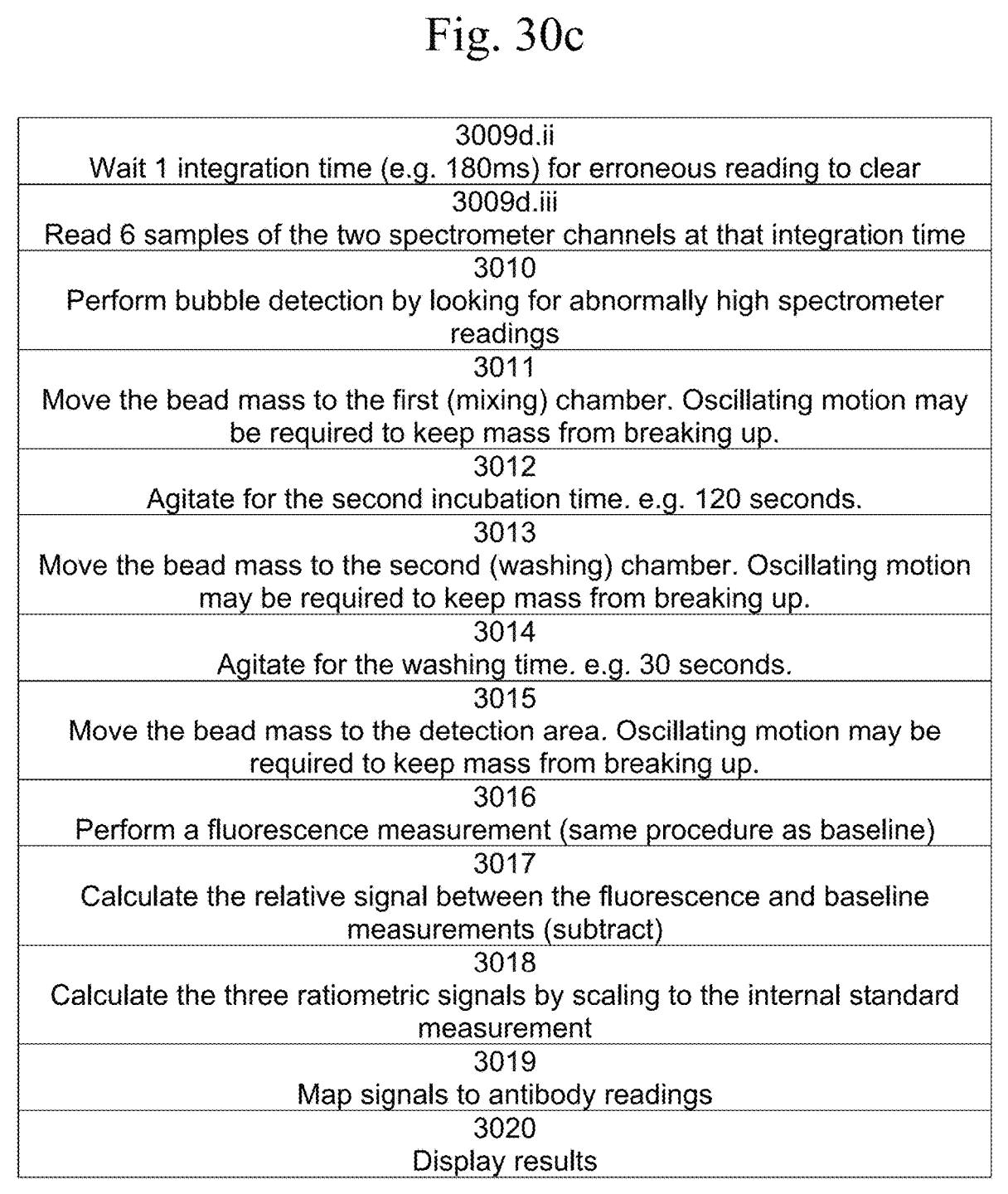

| |
|---|
| 3009d.ii<br>Wait 1 integration time (e.g. 180ms) for erroneous reading to clear |
| 3009d.iii<br>Read 6 samples of the two spectrometer channels at that integration time |
| 3010<br>Perform bubble detection by looking for abnormally high spectrometer readings |
| 3011<br>Move the bead mass to the first (mixing) chamber. Oscillating motion may be required to keep mass from breaking up. |
| 3012<br>Agitate for the second incubation time. e.g. 120 seconds. |
| 3013<br>Move the bead mass to the second (washing) chamber. Oscillating motion may be required to keep mass from breaking up. |
| 3014<br>Agitate for the washing time. e.g. 30 seconds. |
| 3015<br>Move the bead mass to the detection area. Oscillating motion may be required to keep mass from breaking up. |
| 3016<br>Perform a fluorescence measurement (same procedure as baseline) |
| 3017<br>Calculate the relative signal between the fluorescence and baseline measurements (subtract) |
| 3018<br>Calculate the three ratiometric signals by scaling to the internal standard measurement |
| 3019<br>Map signals to antibody readings |
| 3020<br>Display results |

CARTRIDGE-BASED AUTOMATED RAPID TEST ANALYZER

CROSS-REFERENCE TO RELATED APPLICATIONS

This application claims the benefit of U.S. Provisional Application No. 63/163,027, filed Mar. 18, 2021, and U.S. Provisional Application No. 63/280,783, filed Nov. 18, 2021, and is a continuation-in-part of U.S. patent application Ser. No. 16/855,709, filed Apr. 22, 2020, which claims the benefit of U.S. Provisional Application No. 62/988,320, filed Mar. 11, 2020, U.S. Provisional Application No. 62/991,906, filed Mar. 19, 2020, U.S. Provisional Application No. 62/993,222, filed Mar. 23, 2020, U.S. Provisional Application No. 62/994,165, filed Mar. 24, 2020, and U.S. Provisional Application No. 63/001,291, filed Mar. 28, 2020, the contents of which are incorporated herein in their entirety.

BACKGROUND

The present invention relates to a rapid test device that provide rapid detection of substances, including those involved in pathogen infection, for example, using Microscale Affinity Chromatography (MAC), indirect ELISA, and optical molecular sensing technology.

For example, COVID-19, a disease caused by the novel coronavirus (SARS-CoV-2) that was first reported from Wuhan, China, on Dec. 31, 2019, has been declared an international pandemic by the World Health Organization. The virus is spread between people who are in close contact with one another through respiratory droplets produced by coughing or sneezing. The incubation period of COVID-19 is approximately 14 days, making it difficult to contain and contributing to its rapid spread. Current detection techniques rely on RT-PCR, which is a lengthy process, necessitating well-equipped laboratories and skilled personnel to perform the technique. Rapid screening methods are needed to detect the disease at points of entry, transportation hubs, schools, hospitals, and other areas at high risk for communicating the disease in order to limit the spread of the virus. Furthermore, rapid methods of assessing a person's immunity to the virus are becoming increasingly important as people plan for returning to schools and workplaces after the peak of the epidemic. The need to assess the efficacy of vaccines in development has been recognized and is essential in assessing the "herd immunity" to prevent a resurgence of the pandemic.

Accordingly, a need arises for techniques for rapid detection of substances, including those involved in pathogen infection.

SUMMARY

Embodiments may include a rapid test device that provide rapid detection of substances, including those involved in pathogen infection, for example, using Microscale Affinity Chromatography (MAC), indirect ELISA, and optical molecular sensing technology.

For example, embodiments may provide pathogen detection using a marked target substance and fluorescence detection for high sensitivity and fast test time. Such test may be on the order of seconds or minutes instead of hours. An embodiments of a test device may be compact and cost effective and may not need to be cleaned or serviced between tests. Embodiments may include sample cartridges that are pre-filled with the necessary compounds and are ready to accept a liquid test sample for immediate testing.

For example, in an embodiment, a system may comprise a cartridge comprising a first chamber configured to receive a test sample including a target substance, the first chamber pre-filled with micromagnetic particles treated so as to bind to the target substance, and a first reservoir pre-filled with at least one reagent labeled with at least one fluorescent compound, the reagent adapted to bind to micromagnetic particles that are bound to the target substance, and an apparatus comprising a light source disposed so as to excite the least one fluorescent compound with a light and an optical sensor disposed so as to detect an emitted spectrum of light from the excited least one fluorescent compound.

In embodiments, the light source may comprise at least one excitation light emitting diode disposed so as to excite fluorescence of the least one fluorescent compound. The optical sensor may comprise at least one photodiode disposed so as to detect the excited fluorescence of the least one fluorescent compound and to output a signal representing the detected fluorescence. The first reservoir may be pre-filled with a plurality of reagents each labeled with a different one of a plurality of fluorescent compounds. The light source may comprise a plurality of excitation light emitting diodes disposed so as to excite fluorescence of the plurality of fluorescent compounds. The optical sensor may comprise at least one photodiode disposed so as to detect the excited fluorescence of the plurality of fluorescent compounds and to output signals representing the detected fluorescences. Each of the plurality of fluorescent compounds may have a wavelength range that does not overlap with at least some of the others of the plurality of fluorescent compounds. The apparatus may further comprise a loading bay disposed on the apparatus to receive the cartridge, a door disposed on the apparatus to cover the loading bay, a plurality of prongs disposed on an interior of the door to provide actuation force to dispense blister reservoirs disposed on the cartridge when the door is closed, and a device disposed relative to the cartridge to move at least a portion of contents of the cartridge among a plurality of chambers of the cartridge. The device disposed relative to the cartridge to move at least a portion of the contents of the cartridge among chambers of the cartridge may comprise a motor having disposed on a drive shaft thereof a pinion, a rack meshed with the pinion, and a magnet disposed on the pinion and disposed relative to the cartridge so as to move at least a portion of the contents of the cartridge among chambers of the cartridge when the motor is driven. Driving of the motor may be controlled by a computer system comprising a processor, memory to store program instructions and data and accessible by the processor, and program instructions stored in the memory and executable by the processor to control driving of the motor.

In an embodiment, a method may comprise illuminating at least one fluorescent compound with a light from a light source so as to excite the least one fluorescent compound and detecting an emitted spectrum of light from the excited least one fluorescent compound with an optical sensor, wherein the at least one fluorescent compound is contained in a cartridge comprising a first chamber configured to receive a test sample including a target substance, the first chamber pre-filled with micromagnetic particles treated so as to bind to the target substance and a first reservoir pre-filled with at least one reagent labeled with the at least one fluorescent compound, the reagent adapted to bind to micromagnetic particles that are bound to the target sub stance.

In embodiments, the light source may comprise at least one excitation light emitting diode disposed so as to excite fluorescence of the least one fluorescent compound. The optical sensor may comprise at least one photodiode disposed so as to detect the excited fluorescence of the least one fluorescent compound and to output a signal representing the detected fluorescence. The first reservoir may be pre-filled with a plurality of reagents each labeled with a different one of a plurality of fluorescent compounds. The light source may comprise a plurality of excitation light emitting diodes disposed so as to excite fluorescence of the plurality of fluorescent compounds. The optical sensor may comprise at least one photodiode disposed so as to detect the excited fluorescence of the plurality of fluorescent compounds and to output signals representing the detected fluorescences. Each of the plurality of fluorescent compounds may have a wavelength range that does not overlap with at least some of the others of the plurality of fluorescent compounds. The method may further comprise moving at least a portion of the contents of the cartridge among a plurality of chambers of the cartridge using apparatus comprising a motor having disposed on a drive shaft thereof a pinion, a rack meshed with the pinion, and a magnet disposed on the pinion and disposed relative to the cartridge so as to move at least a portion of the contents of the cartridge among chambers of the cartridge when the motor is driven. Driving of the motor is controlled by a computer system comprising a processor, memory to store program instructions and data and accessible by the processor, and program instructions stored in the memory and executable by the processor to control driving of the motor.

BRIEF DESCRIPTION OF THE DRAWINGS

The details of the present invention, both as to its structure and operation, can best be understood by referring to the accompanying drawings, in which like reference numbers and designations refer to like elements.

FIG. 10 is an exemplary block diagram of a test cartridge according to embodiments of the present techniques.

FIG. 22 is an exemplary flow diagram of reagent processing according to embodiments of the present techniques.

FIG. 29 is an exemplary flow diagram of a process of operation according to embodiments of the present techniques.

FIG. 30*a* is a portion of an exemplary flow diagram of a process of operation according to embodiments of the present techniques.

FIG. 30*b* is a portion of an exemplary flow diagram of a process of operation according to embodiments of the present techniques.

FIG. 30*c* is a portion of an exemplary flow diagram of a process of operation according to embodiments of the present techniques.

DETAILED DESCRIPTION

Figure 1:
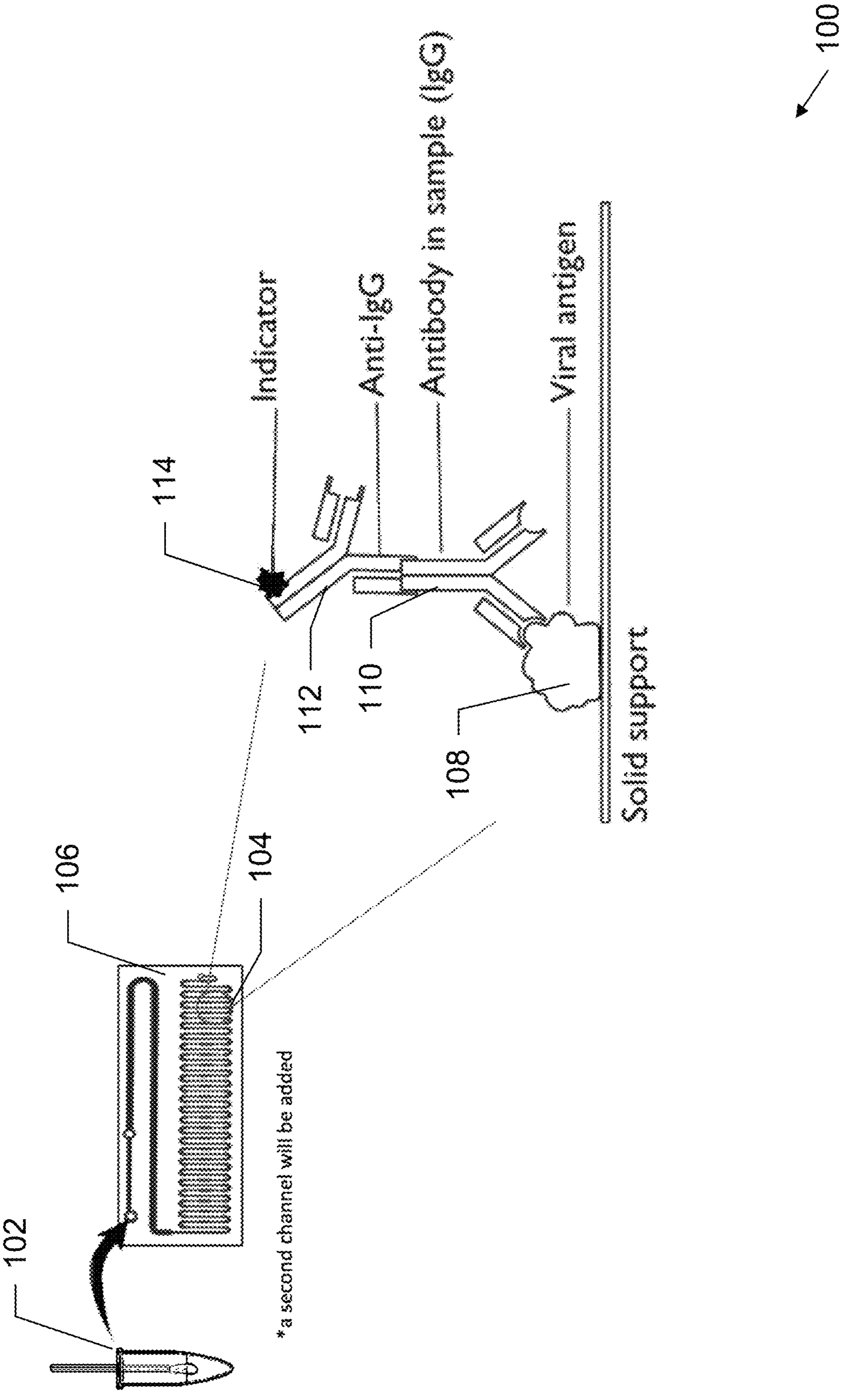
FIG. 1 is an exemplary schematic representation of viral detection. according to embodiments of the present techniques.

Embodiments may include techniques that provide, rapid detection of COVID-19 infection and techniques for rapid assessment of a person's immunity to the virus. For example, embodiments of the present techniques may provide rapid, accurate antibody and viral load testing using Microscale Affinity Chromatography (MAC), indirect ELISA, and optical molecular sensing technology.

Due to the nature of the coronavirus and its ability to spread quickly, there is an immediate need for a portable, instant, non-invasive test that does not require skilled technicians or lab equipment. Currently, only patients who experience severe symptoms are tested in hospitals because tests are too expensive and short in supply. Meanwhile, unscreened patients who have mild or no symptoms continue their daily life, increasing the scale of contamination. The current gold standard for SARS-CoV-2 detection is real time RT-PCR (reverse transcription-polymerase chain reaction). The drawbacks of RT-PCR are multi-faceted in that the equipment is expensive, conducting tests requires expertise, and results take hours to acquire. A complete reaction can be performed in as little as 4 hours, however, the collection of samples, transportation to the lab, preparation of equipment and analysis of results mean significantly longer time is required. Increasing demand for samples to be tested, along with a limited supply of reagents, skilled staff and equipment, can extend the entire RT-PCR process from sample collection to final result to several days. Furthermore, not only is RT-PCR time consuming (average turnaround 3-6 days), but it is also highly labor and cost intensive charging patients and insurance companies up to $4,000 per test. Therefore, there is a recognized need for more rapid, inexpensive tests.

More rapid diagnostic tests have recently come to the market. However, these tests lack reproducibility and have a higher risk of providing false positives. These technologies also utilize forms of sampling that require proximity to the patient, leaving healthcare workers at a higher risk of contracting the disease, such as a nasotracheal swab or a blood sample. The risk to healthcare workers can be minimized by simply acquiring a pooled saliva sample, as SARS-CoV-2 has been detected in saliva of infected patients.

Additionally, evidence shows that convalescent plasma from patients who have recovered from viral infections can be used as a treatment for infection without severe adverse events. The rationale behind convalescent plasma therapy is that the antibodies from a recovered patient's serum might suppress viraemia in an ill patient. The ability to quickly screen recovered patients and administer their convalescent plasma to ill patients is an area lacking in proper diagnostic tests.

After the threat of the pandemic has been mitigated, a need to screen the population to assess the efficacy of vaccines towards the virus to build "herd immunity" has been recognized. Herd immunity (also called community immunity) is an important mechanism by which the larger community is protected. For some diseases, if enough people are immune, transmission of the disease is reduced or eliminated. In the case of protecting against a resurgence of another global pandemic, herd immunity will need to be assessed to determine vulnerable sites with the potential to become hotspots.

Embodiments of the present techniques may include a process to rapidly detect COVID-19 through an alternative method of testing crude saliva samples. Embodiments may utilize lab-on-a-chip technology, where a patient sample containing saliva may be analyzed for antibodies capturing the virus with a simultaneous release of a fluorescent marker ligand. The lab on a chip technology may have the capability to produce a read out in real time using a fluorescent marker passing through a fluorometer. The lab on a chip technology may provide reusable capability, allowing for multiple testing opportunities from one device.

Embodiments may provide a completely self-contained device, with single-use sampling chips, which will reduce the risk of carry-over and minimize error as the sample does not have to be handled after it is loaded. All reagents needed for buffering, dilutions, or washing may be fully contained in a multiple use cartridge, which can be replaced or refilled as needed. Embodiments may be utilized at transportation hubs, such as airports, schools, clinics, and hospitals to limit the spread of the virus, and the technology may be expanded to screen for immunity towards other infectious diseases. In embodiments, the sampling chips and devices may be designed to concurrently detect the presence of both antibodies and virus in the same sample by utilizing the methods described below on the same sampling chip and in the same device.

In embodiments, the testing device may be an automated sandwich immunoassay with fluorescence detection intended for detection of IgA, IgM, IgG antibodies toward SARS-CoV-2 in patients with an active immune response to the virus. Results may identify an immune response to SARS-CoV-2. The screened antibodies are generally detectable in saliva during all phases of infection. Positive results from the embodiments of the testing device are indicative of an active immune response to the virus, that is, that an individual has been infected with SARS-CoV-2 and facilitated a targeted immune response to the virus.

In embodiments, the testing device is intended for use by consumers, clinicians, and point-of-care facilities. In embodiments, the testing device may be used by a variety of consumers in both traditional healthcare settings and elsewhere, for example, in clinics and hospitals, point of entry locations, and private settings, such as at home and in commercial locations. A trained technician is not required to operate the device, and results can easily be read by both licensed healthcare professionals and private individuals. Such access significantly increases the likelihood to determine transmission, resulting on an immediate impact on local and global health.

Embodiments may include a self-contained device that may utilize single-use disposable test cartridges, containing microfluidic chips. Each disposable test cartridge may be self-contained, and the sample may be magnetically moved through the cartridge's microfluidic chip. The test cartridge comes with all necessary reagents, and cleaning supplies are not applicable due to the disposable nature of the cartridges. Additional testing cartridges can be ordered as needed.

Embodiments may include a testing device utilizing automated sandwich immunoassay with fluorescence detection in a microfluidic device for the detection of anti-SARS-CoV-2 IgA, IgM, and/or IgG antibodies in saliva samples. S1 protein from the SARS-CoV-2 virus or a mixture of proteins or their subunits from the virus may be immobilized on, for example, magnetic particles. The magnetic particles may be moved through the use of electromagnets to mix with the saliva sample. In embodiments, magnetic particles that may be used may include, for example, Epoxy Silica Magnetic Particles, 6 μm, Ni-NTA Silica Magnetic Particles, 6 μm, etc.

Embodiments may use the principle of a sandwich immunoassay on magnetic beads. Spike protein specific to the SARS-CoV-2 virus or a subunit of this protein may be immobilized on the surface of silica-coated magnetic beads. Anti-SARS-CoV-2 IgA, IgM, or IgG antibodies from the saliva sample will attach to the antigen immobilized on these beads. Examples of the antigen may include a recombinant SARS-CoV-2 spike protein or the s1 subunit of the spike protein, etc., these proteins may be his-tagged. The magnetic particles will be moved through the cartridge to mix with secondary antibodies labeled with a fluorescent molecule. Examples of fluorescent molecules may include QUANTABLU™ Fluorogenic Substrate, having an excitation maximum at about 325 nm and an emission maximum at about 420 nm, QUANTARED™ Enhanced Chemifluorescent Substrate having an excitation maximum at about 570 nm and an emission maximum at about 585 nm, fluorescein: having an excitation maximum in a range of about 475-495 nm and an emission maximum in a range of about 510-520 nm, etc. The anti-IgA, anti-IgM, and anti-IgG secondary antibodies will serve to detect the binding of antibodies from a positive sample to the immobilized spike protein. Examples of antibodies may include anti-Goat IgG, anti-Goat IgG-FITC labeled, anti-human IgG, anti-human IgM, anti-rabbit IgG, anti-rabbit IgG-FITC labeled, etc. After a wash step with a neutral buffer, to remove excess antibodies, the beads may be moved under a fluorescence detector in the device to detect the signal. Examples of buffers may include tris-buffer, pH ~7 (for wash), phosphate buffer, pH ~7 (for wash), etc. A solution of 10 N HCl may be used for regeneration of the cartridge if desired.

The antibodies raised against SARS-CoV-2 that are present in the saliva from patients with an active immune response to the virus will bind to the immobilized antigen on the particles. The magnetic particles will then be mixed with a fluorescent-labeled secondary antibody, which will bind to anti-virus antibodies, which were present in the sample. In embodiments, the magnetic particles will then be passed into a washing area, then passed under a fluorescent detector, which will detect the signal.

In embodiments, the results may be indicated by a colored light, such as green, yellow or red. Green indicates a positive result, meaning anti-SARS-CoV-2 antibodies have been detected at or above a level that represents current or past infection by SARS-CoV-2 and an active immune response. Yellow indicates an indeterminate result (i.e., user error), and red indicates a negative result, meaning that no anti-SARS-CoV-2 antibodies are present.

In embodiments, testing device capacity may be, for example, several hundred tests per day. In embodiments, the total time required to perform the test may be, for example, five (5) minutes. In embodiments, the number of tests that can be performed per testing device may be one per run.

In embodiments, the estimated shelf life of reagents may be approximately six (6) months with refrigeration. Without refrigeration, shelf life is expected to be shortened, but still likely to be suitable for intermediate to long-term use, for example, approximately three (3) to six (6) months. In embodiments, nM concentrations of antibodies may be used, which are typical concentrations for enzyme based assays. Specific materials to be used may include IgA, IgM, and/or IgG antibodies. Cross-reactivity with other pathogens or antibodies towards other pathogens is not expected. The S1 subunit of the SARS-CoV-2 virus is expected to react specifically with antibodies against the virus.

Detection of Antibody. Embodiments may provide a rapid COVID-19 screen that utilizes a sandwich assay or indirect enzyme-linked immunosorbent assay (ELISA) method. A sandwich immunoassay is a method using two antibodies, which bind to different sites on the antigen or ligand, as shown in FIG. 1. The capture antibody, which is highly specific for the antigen, is attached to a solid surface. The antigen is then added, followed by addition of a second antibody referred to as the detection antibody. The detection antibody binds the antigen at a different epitope than the capture antibody. As a result, the antigen is 'sandwiched' between the two antibodies.

Figure 18:
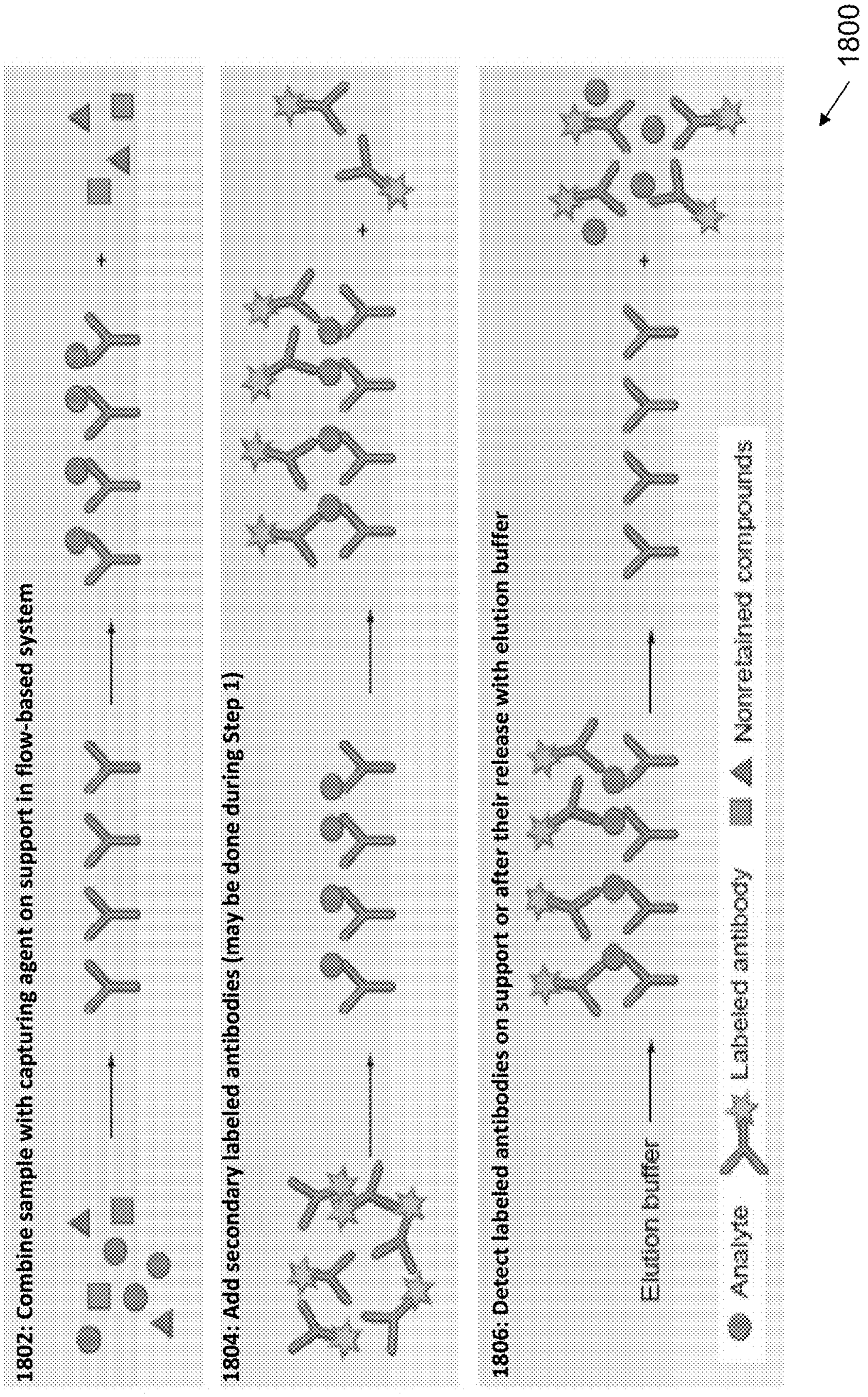
FIG. 18 is an exemplary block diagram of a process of flow-based sandwich immunoassay according to embodiments of the present techniques.

An overview of a flow-based sandwich immunoassay process 1800 according to the present systems and methods is shown in FIG. 18. In process 1800, a Sandwich Immunoassay may be conducted based on two antibodies and binding agents to measure a target compound located in the cartridge of the device. At 1802, a sample may be sample with a first binding agent on a support in a flow-based system. For example, The first binding agent, a COVID-19 (SARS-CoV-2) specific antigen, may be attached to magnetic beads and may be used to capture the anti-COVID-19 IgA, IgM, and IgG antibodies from the saliva sample. At 1804, one or more secondary labeled antibodies may be added (this may instead be done at 1082). Each secondary antibody may contain a fluorescent label that will be used to detect and measure the amount of the capture agent. At 1806, labeled antibodies may be detected, either on the support or after their release with an elution buffer. This approach is highly advantageous as it allows for the detection of any stage of infection (early/late/resolved) by identifying at least three isotypes of antibodies.

As shown in FIG. 1, a crude saliva sample 102 may be injected into a capillary 104 etched onto a silica microfluidic chip 106. For example, saliva may be collected into a 1 mL sterile tube, such as an Eppendorf tube, and transferred with a sterile plastic Pasteur pipette, which will be included with the cartridge. This device is already FDA cleared and widely available. In embodiments, once the cartridge with the saliva sample is put into the device, the remaining steps may be performed automatically by the device. The anti-SARS-CoV-2 antibodies in the sample will be selectively separated by the magnetic beads with spike protein antigen attached. Any particulate matter will be left behind in the initial port where the sample is introduced. In embodiments, there is no sample preparation that needs to be done by the user.

Capillary 104 contains an immobilized SARS-CoV-2 specific antigen 108 to detect SARS-CoV-2 specific antibodies in the sample. If a sample contains antibodies towards the virus, indicating an immune response has occurred, these antibodies 110 will attach to the immobilized antigen. After the sample is run through the capillary, a detection reagent containing a secondary antibody 112 tagged with a fluorescent fluorophore 114 will be introduced. Secondary antibody 112 will recognize blood or saliva-borne antibodies 110 which have attached to immobilized antigen 108. A fluorometer (not shown) will then detect whether secondary antibody binding has occurred. A fluorometer may be used to measure parameters of visible spectrum fluorescence such as its intensity and wavelength distribution of emission spectrum after excitation by a certain spectrum of light. This is described further below with reference to FIG. 4.

This approach is highly advantageous as it allows for the detection of any stage of infection (early, late or resolved) by identifying three isotypes of antibodies.

Immobilization of Antigen. Embodiments may include disposable silica chips 106 be pre-packaged with SARS-CoV-2 specific antigen 108, preferably the S1 protein, directly immobilized onto etched capillaries or onto magnetic particles or beads. Antigen will be diluted in binding solution (0.2 M carbonate-bicarbonate), added to the chip, and incubated. Deactivated surfaces will be used to prevent the need for a blocking step to prevent the non-specific binding of antibodies to the chip. The user need only collect a crude saliva sample, which can then be introduced to the column for detection.

Use of Saliva Sample. Not only is the use of pooled saliva less invasive than blood or nasopharyngeal swabs, but it also minimizes exposure for healthcare workers. Some virus strains have been detected in saliva as long as 29 days after infection. SARS-CoV-2 can present in the saliva in at least three ways. First, SARS-CoV-2 in the lower and upper respiratory tract can enter the oral cavity with the liquid droplets frequently exchanged by these organs. Second, SARS-CoV-2 in the blood can access the mouth via crevicular fluid. Third, major- and minor-salivary gland infection, with subsequent release of SARS-CoV-2 particles in saliva via salivary ducts can cause SARS-CoV-2 to present in the saliva.

Recent tests for other viral diseases, such as HIV, are employing saliva in a similar fashion as they have advantages over blood-based tests in terms of quality, rapidity and convenience. The sensitivity, specificity, positive predictive value and negative predictive value of such HIV tests may be quite high.

Pooled saliva samples can be used to detect both IgG and IgM antibodies, which pass into the mouth through the mucosa, and IgA which are secreted in the mouth. The production of IgM, IgA and IgG antibodies against COVID-19 were found in patient serum as early as day 1 after symptom onset. IgA antibodies were detected in 92.7% of patient samples collected within 0-7 days of symptom onset. IgM and IgA antibodies were both detectable at day 5, and the detection time of IgM, IgA, and IgG against COVID-19 ranged from day 1 to 39 PSO.

One study found the sensitivity and specificity of a lateral flow kit utilizing blood to detect COVID-19 IgM and IgG was 88.66% and 90.63%, respectively (Li, Z., et al., 2020). As the present techniques will additionally test IgA, and since the profile of antibodies in the saliva is similar to that in blood, embodiments of the present techniques should yield similar, if not higher, sensitivity and specificity, as well as a higher accuracy in detecting patients at any stage of infection.

Detection of Antibody. Along with the crude saliva sample, a detection reagent including a secondary antibody labeled with a fluorophore will be introduced to the chip. In embodiments, non-captured sample components and any non-bound secondary antibody can be effectively washed from the device using an application buffer, with the possible use of additives to minimize non-specific binding, as antibodies against the viral antigen are captured by the support. Alternatively, in embodiments, the sample may be applied first to the support, followed by application of the labeled secondary antibodies, with the non-captured or non-bound components again being washed from the support during this process. The conjugated antibodies that are used for this process may be obtained from existing sources or prepared according to well-established procedures for adding fluorescent tags to antibodies or other secondary binding agents. The performance of this device over extended use can be monitored by analyzing positive and negative control samples along with samples.

In addition to detecting immunity, embodiments may be used to verify vaccine immunogenicity. Embodiments may assist researchers in assessing whether the correct antibody profile necessary to protect a patient from reinfection is present. The overall estimated effectiveness of seasonal influenza vaccine for preventing medically attended, laboratory-confirmed influenza virus infection in the 2019 to 2020 flu season was only 45% (Dawood, F. S., et al.). In clinical trials, this method can be used to confirm that antibodies have been raised to the pathogen, meaning the patient has had effective coverage from infection with the pathogen, and has been applied in confirming the effectiveness of the rabies vaccine in dogs and cat (Servat, A., et al., 2007). In addition, immunity to multiple diseases can be screened using a tunable laser and different fluorescent markers.

Figure 3:
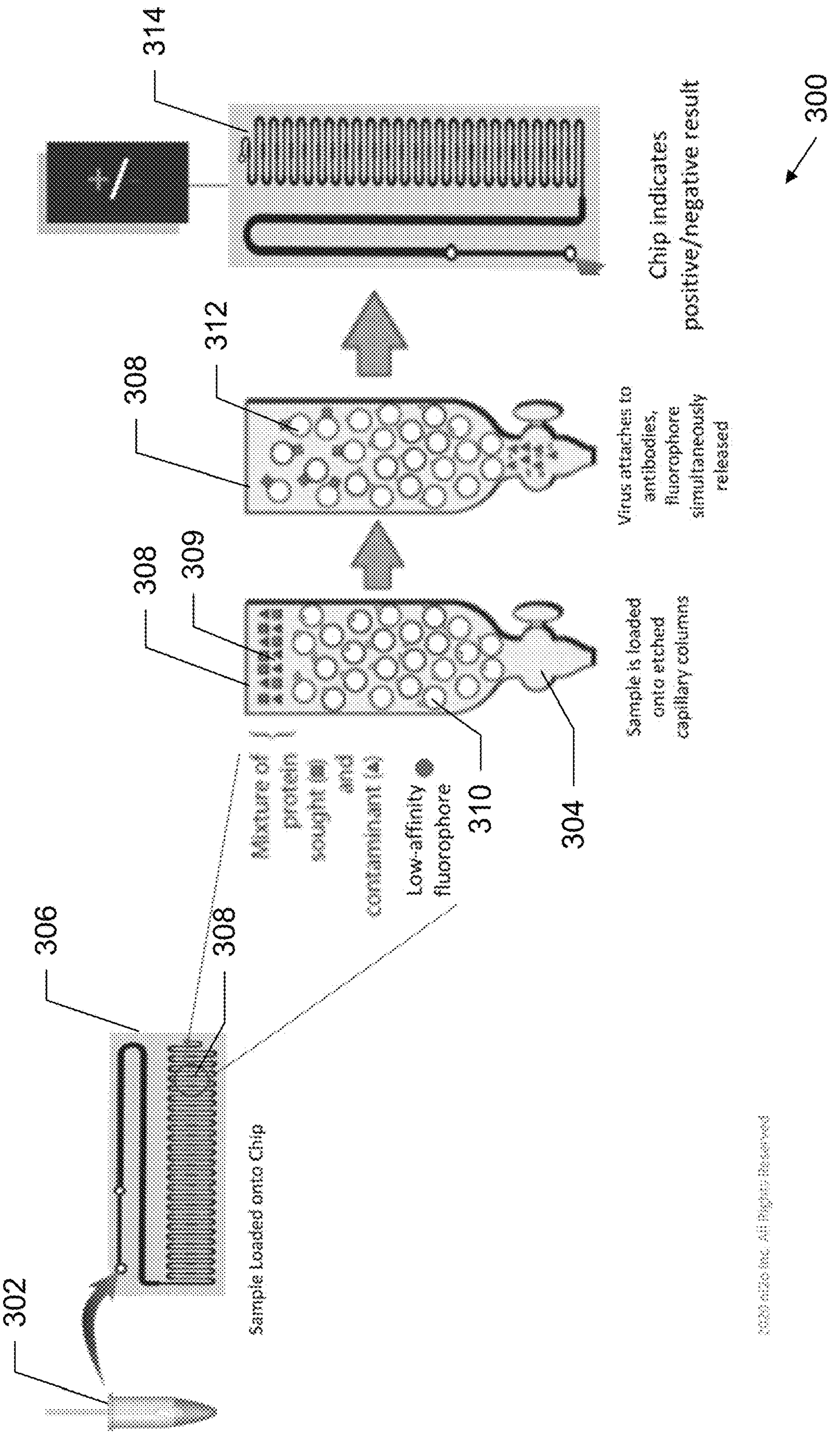
FIG. 3 is an exemplary block diagram of Microscale Affinity Chromatography (MAC) according to embodiments of the present techniques.

Rapid COVID-19 Viral Detection. Embodiments may combine viral detection and antibody detection onto one device, or embodiments may provide stand-alone viral or antibody detection product depending on the needs of the market. In embodiments, a rapid COVID-19 viral detection test may employ Microscale Affinity Chromatography (MAC) technology, a separation technique that combines the specificity of antibody recognition and binding with the power, efficiency and speed of modern liquid-phase separations. An example of Microscale Affinity Chromatography 300, according to embodiments of the present techniques, is shown in FIG. 3. A saliva sample 302 is loaded 304 onto a silica microfluidic chamber 306 etched with columns 308 on which primary antibodies 309 towards SARS-CoV-2 are immobilized. Low-affinity fluorophores 310 are weakly bound to these antibodies and are displaced 312 when a sample containing SARS-CoV-2 is introduced. Displaced fluorophores 312 can be considered an indication of a positive result.

In embodiments, antibodies 309 towards SARS-CoV-2 specific proteins will be immobilized on the surface of micro-capillaries 308, microcolumns or etched silica channels on a lab-on-a-chip technology and then tagged with a low affinity competitive ligand 310 containing a fluorophore. A crude patient sample 302, such as saliva, oral or nasopharyngeal swab or blood, can be introduced onto the channel 308 and migrated through the device either by electric charge or a flow system. If SARS-CoV-2 is present in the sample, the virus antigens will be captured on the columns 312 by the antibodies 309 releasing the low affinity ligand 310 to the end of the column. The viral antigens in sample 302 have a higher affinity or liking for the antibodies 309 and therefore will bind to the antibodies 309 and elute the ligand 310 which has a lower affinity. If the low affinity ligands 310 are released from the antibodies 309, a fluorescent marker ligand 310 will be released to indicate a positive sample. If no fluorescence is seen, the sample is negative, because the low affinity ligand 310 was never released from the antibodies.

Sampling. Due to ease of sampling, and lack of necessity for sample preparation, embodiments may use a crude saliva sample 302. The subject will spit into a tube, and a plastic pipette or dropper may be used to transfer the saliva to the etched chip 306. Embodiments may use alternative sampling techniques, such as a nasopharyngeal swab, oral swab or blood sample. In embodiments, a breathalyzer may be interfaced with the COVID-19 detection device. In embodiments, samples from surfaces or air may also be tested using swab methods, or air sampling methods, respectively.

Although the example of Microscale Affinity Chromatography shown in FIG. 3 is described in terms of detection of SARS-CoV-2, the described techniques and apparatus are equally applicable to detection of other pathogens, such as viruses, bacteria, etc.

Figure 2:
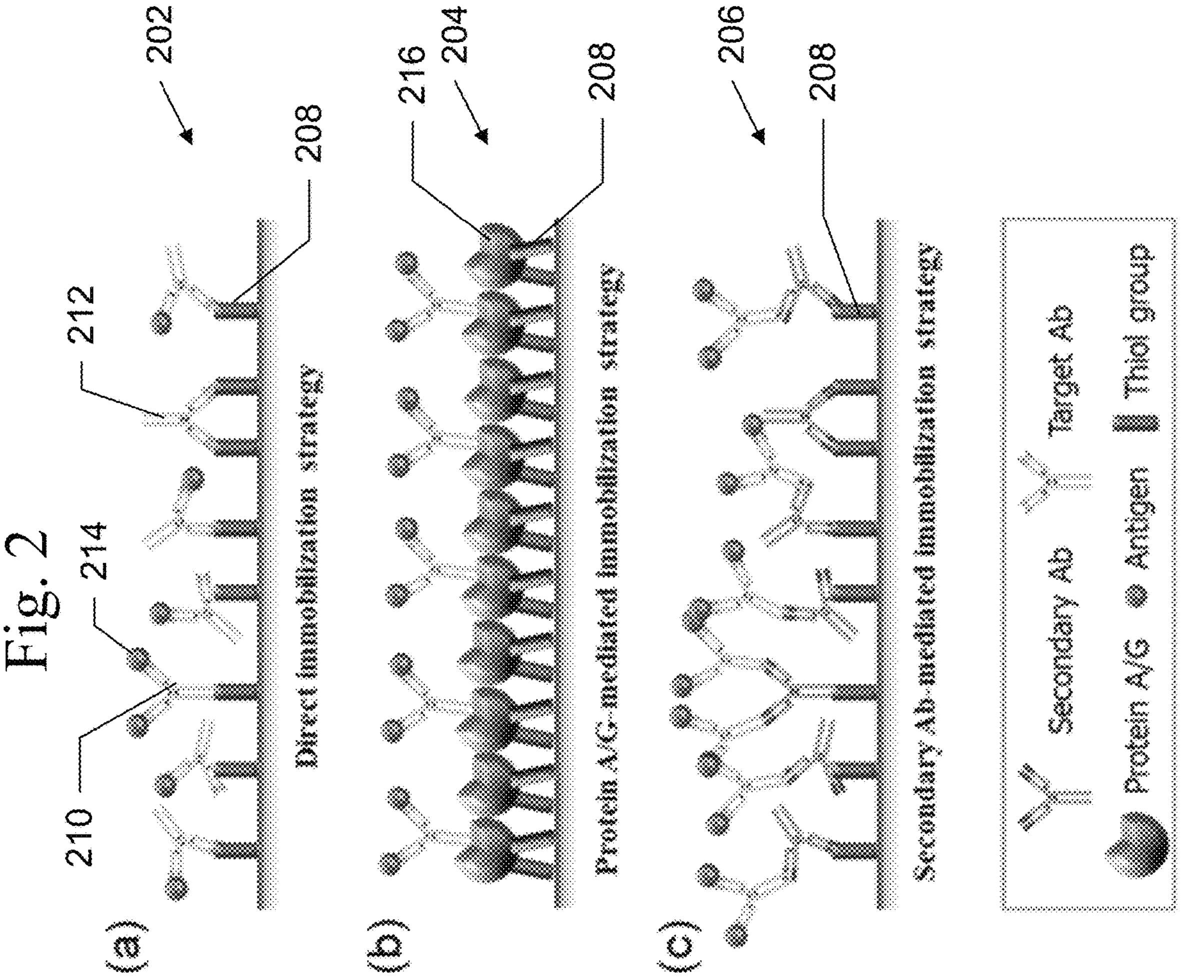
FIG. 2 are exemplary schematic representations of target antibody immobilization on a surface according to embodiments of the present techniques.

Antibody Immobilization to Silica Chip. Exemplary schematic representations of target antibody immobilization on surface, such as gold, using (a) direct target antibody 202, (b) protein A/G-mediated 204, and (c) secondary antibody-mediated immobilization strategies 206 are shown in FIG. 2. In embodiments, antibodies can be attached directly 202 to the walls of a capillary column or microchip channel, however, the orientation of the stationary antibody is key to the binding activity. Antibodies can be immobilized covalently, using a thiol group 208, to a surface or connected to a solid support, although the oriented immobilization of antibodies is considered to be optimal for their effectiveness. An antibody is considered to be properly oriented and perfectly active 210 when the fragment crystallizable region (Fc), which has no antigen binding affinity, is immobilized on a surface, rather than the antigen-binding sites 214 being immobilized on the surface 212. This situation can be produced by a covalent immobilization method, such as carbohydrate groups in an antibody's Fc region. Directly immobilized antibodies do not allow for specific orientation of the antibody, thus, embodiments may use other methods to immobilize antibodies to a silica microfluidic chip, as described below.

It is also possible to achieve proper immobilization through secondary molecule protein A/G-mediated immobilization 204, or secondary Ab-mediated immobilization 206. In protein A/G-mediated immobilization 204, the biomolecules used for antibody immobilization are proteins A and G 216. Protein A is the most successful surface protein able to bind with animal immunoglobulin G (IgGs), but is not effective in certain animal IgGs, such as goat, sheep, cow, and horse. Protein G reacts more with IgGs than protein A and reacts less with other antibody types. A recombinant protein A/G that combines four immunoglobulin-binding domains from protein A and two from protein G can be employed to modify silane-functionalized silicon nitride surfaces.

In Ab-mediated immobilization 206, secondary antibodies 218 are attached to the support and used to recognize the Fc region of the primary antibodies against the target. In this situation, the binding ability of the secondary antibodies should match with the class or subclass of the primary antibody that is to be used immobilized. For example, if the primary antibody is one of mouse IgG subclasses or rabbit IgG, an anti-mouse IgG or anti-rabbit IgG could be used as secondary antibodies. After immobilizing the thiolated-secondary antibody on a silica surface, the target antibody can be captured by the secondary antibody in the correct orientation by binding between the Fab region of the secondary antibody and the Fc region of target antibody.

The example of target antibody immobilization on surface shown in FIG. 2 is not described in terms of detection of any particular pathogen. Rather, the described techniques and apparatus are applicable to detection of many pathogens, such as viruses, such as SARS-CoV-2, bacteria, etc.

Primary Antibody. There are 4 conserved structural proteins across CoVs: the spike (S) protein, membrane (M) protein, envelope (E) protein, and nucleocapsid (N) protein. The S protein is responsible for binding to host cell receptors and viral entry to host cells. The M, E, and N proteins are part of the nucleocapsid of viral particles. S and N genes are under episodic selection as the virus is transmitted between humans. Mutations and adaptation in the S and N genes may affect virus stability and pathogenicity.

Embodiments may use a single primary antibody towards a conserved portion of any of the aforementioned proteins can be used, or embodiments may use a mixture of primary antibodies, which are specific to different mutations of the virus. Monoclonal antibodies towards a conserved portion of the S1 spike surface proteins of SARS-CoV-2 may be a primary target of embodiments. However S2, M, E, or N antibodies may be tested in embodiments.

Figure 4:
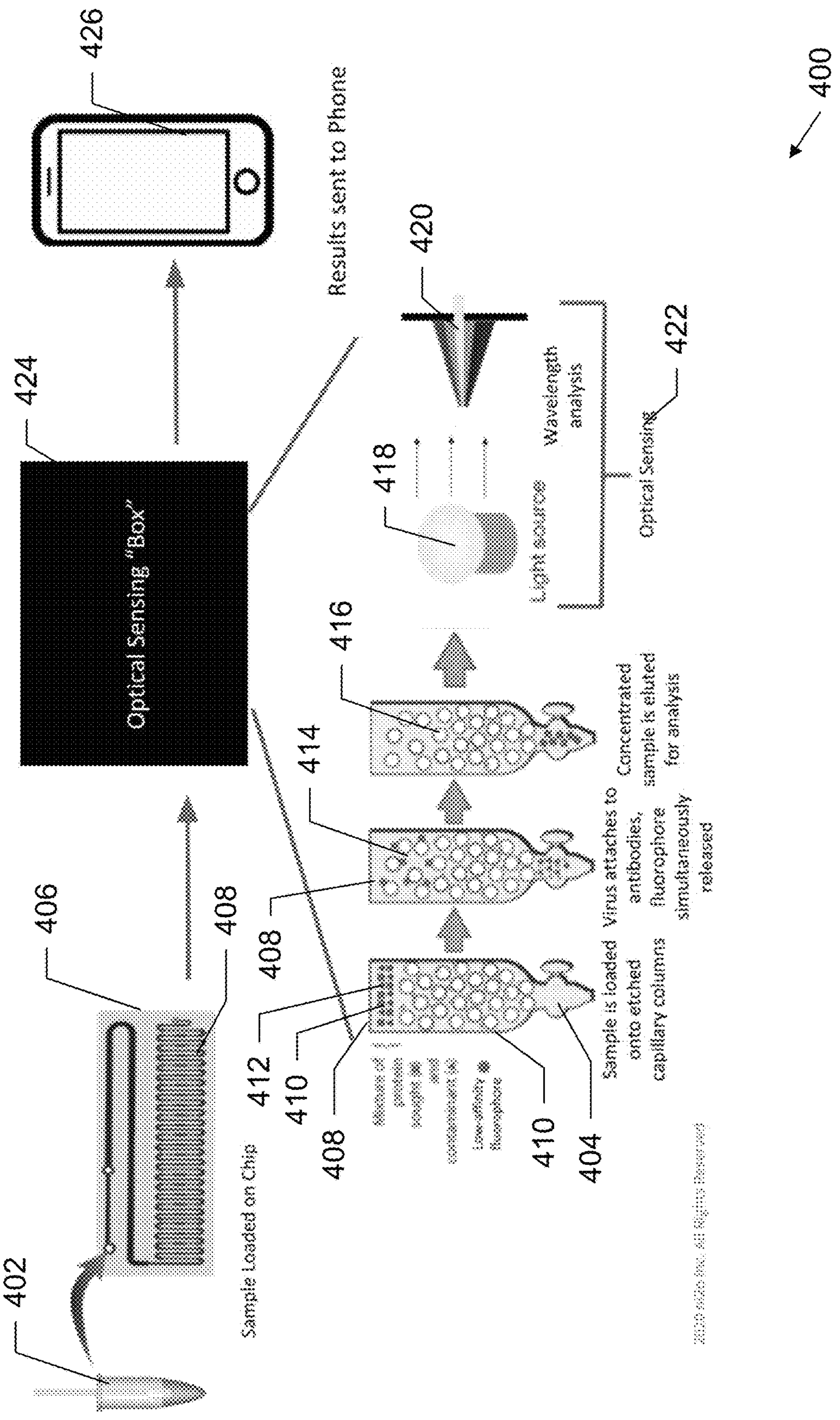
FIG. 4 is an exemplary schematic representation of optical detection according to embodiments of the present techniques.

An example of Microscale Affinity Chromatography with Competitive Affinity Ligand and optical sensing 400, according to embodiments of the present techniques, is shown in FIG. 4. A saliva sample 402 is loaded 404 onto a silica microfluidic chamber 406 etched with columns 408 on which primary antibodies 410 towards SARS-CoV-2 are immobilized. In embodiments, a low-to-moderate affinity, competitive ligand fluorophore 412 will be attached to the primary antibody 410 before the sample 402 is run through the column 408. This fluorescent compound will attach to the primary antibody immobilized on the chip, as visualized in FIG. 2. As the sample 402 is run 414 through the column 408, SARS-CoV-2 within the sample will compete for binding to the primary antibody 410 and, because it has a higher affinity towards the antibody 410, will displace the fluorophore 412. The displaced fluorophore 412 will then be used as an indication of a positive result, and lack thereof can be regarded as a negative result. The concentrated sample may then be eluted 416 for analysis.

In embodiments, fluorescein, a xanthene dye that is highly fluorescent, and detectable even when present in minute quantities may be used. Embodiments may use one of numerous fluorescent markers that are available to serve this function. For example, fluorescein has an excitation maximum in a range of about 475-495 nm and emission in a range of about 510-520 nm, QUANTABLU™ Fluorogenic Substrate, has an excitation maximum at about 325 nm and an emission maximum at about 420 nm, QUANTARED™ Enhanced Chemifluorescent Substrate having an excitation maximum at about 570 nm and an emission maximum at about 585 nm, etc.

Rapid Optical Detection and Improved Sensing. In embodiments, after the concentrated sample containing the biomolecules of interest is eluted 416, additional analysis may be performed using a novel lab-on-chip utilizing wavelength backscattering with at least two wavelengths of light. For example, a light source 418 capable of emitting at least two wavelengths of light, such as a plurality of light emitting diodes, laser diodes, or other lasers, or a tunable laser, may be used to illuminate the eluted sample, exciting the fluorophore 412 and causing light emission 420. The emission spectrum of the light emitted 420 from the fluorophore 412 may be optically sensed 420 and analyzed by, for example, an optical sensing "box" or circuit 422. Optical sensing circuit 422 may perform wavelength and amplitude analysis on the emitted light 420 and may determine the absence, presence, and/or quantity of SARS-CoV-2, or other pathogen, or antibody in the sample 402. In embodiments, such determination may be made in optical sensing circuit 422 and communicated to a computing device 426, such as a smartphone, tablet computer, laptop computer, personal computer, workstation computer, cloud computing service, etc. In embodiments, optical sensing circuit 422 generate data representing the performed wavelength and amplitude analysis and may transmit that data to a computing device

426, such as a smartphone, tablet computer, laptop computer, personal computer, workstation computer, cloud computing service, etc., for determination of the absence, presence, and/or quantity of SARS-CoV-2, or other pathogen, or antibody in the sample 402.

Figure 5:
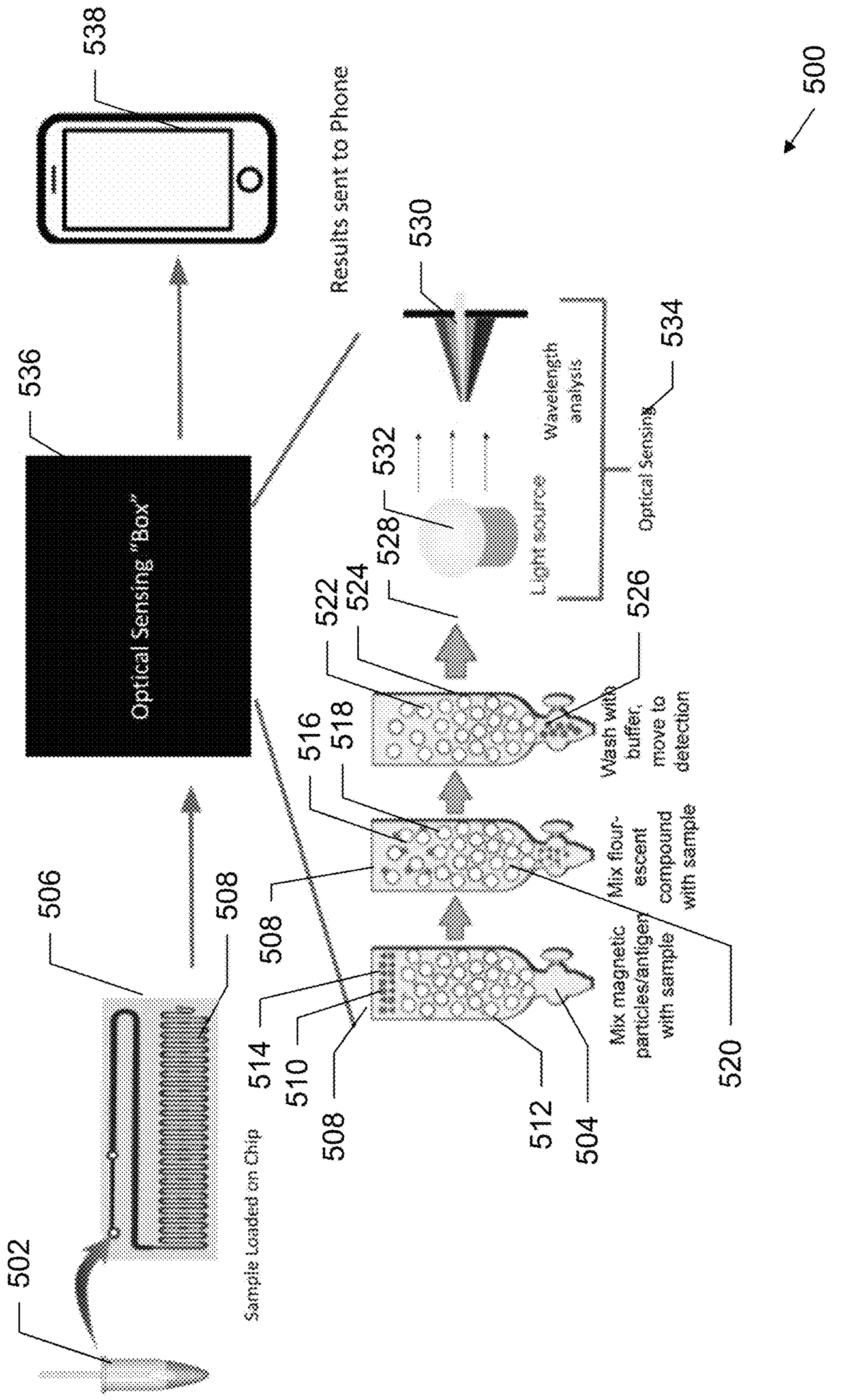
FIG. 5 is an exemplary schematic representation of optical detection according to embodiments of the present techniques.

An example of an embodiment of detection of antibodies raised against SARS-CoV-2 with optical sensing 500, according to embodiments of the present techniques, is shown in FIG. 5. It is best viewed in conjunction with FIG. 6, which is a flow diagram of an embodiment of the testing process 600. Process 600 begins with 602, in which a saliva sample 502 may be collected. The specimen volume may, for example, be less than 1 mL. For example, saliva may be collected into a 1 mL sterile tube, such as an Eppendorf tube, and transferred with a sterile plastic Pasteur pipette. In embodiments, once the cartridge with the saliva sample is put into the device, the remaining steps may be performed automatically by the device.

At 604, particulate matter may be removed from the sample 502 during sample preparation. In embodiments, the anti-SARS-CoV-2 antibodies in the sample will be selectively separated by the magnetic beads with spike protein antigen attached. Any particulate matter will be left behind in the initial port where the sample is introduced. In embodiments, there is no sample preparation that needs to be done by the user. At 606, a portion of saliva sample 502 may be introduced 504 into the cartridge loaded 506 including at least one silica microfluidic chamber 508. For example, about 20-100 μL of the sample 502 may be introduced 504 into the cartridge 506. In embodiments, only a crude approximation of the sample and insertion of the sample by a sterile disposable pipette is necessary. The device may only accept a controlled amount of sample (~30 μL), so the amount of sample measured by the user and inserted into the device need to be exact. The pipette may collect at least 100 μL, which is more than needed. The excess saliva may be discarded with the pipette.

At 608, cartridge 506 may be inserted into the device, and magnetic particles 510 in the cartridge may be moved to the sample in chamber 508 and mixed 512 with the sample. Magnetic particles 510 may have one or more antigens 514 to antibodies raised against SARS-CoV-2 immobilized on the particles. Antibodies present in the sample will bind to the antigens 514 immobilized onto magnetic particles 510. Magnetic particles 510 may be moved by application of electric current by testing device circuitry to magnetic coils. In embodiments, the magnetic coils may be formed on cartridge 506. In embodiments, the magnetic coils may be present in the test device and may be adjacent to or in the vicinity of cartridge 506.

At 610, secondary antibodies (such as IgA, IgM, and IgG) 516 labeled with a fluorescent compound 518, such as fluorescein, QUANTABLU™, QUANTARED™, etc., will also be combined 520 with the magnetic particles and mixed to detect captured antibodies from the sample. At 612, the magnetic particles 510 with attached IgA, IgM, and IgG 516 and fluorescent compound 518, together indicates as 522, may be moved to a washing station 524, and washed 526 using a neutral buffer. At 614, the magnetic particles, etc. 522 may be moved to a detection region 528 to obtain the signal 530 from the fluorescent compound 518 labelling the secondary antibodies 516 on the magnetic particles 510. Antibody isotypes may be distinguished using the color or light emission spectrum of fluorescent compound attached to the secondary antibody.

In embodiments, fluorescein, a xanthene dye that is highly fluorescent, and detectable even when present in minute quantities may be used. Embodiments may use one of numerous fluorescent markers that are available to serve this function. For example, fluorescein has an excitation maximum in a range of about 475-495 nm and emission in a range of about 510-520 nm, QUANTABLU™ Fluorogenic Substrate, has an excitation maximum at about 325 nm and an emission maximum at about 420 nm, QUANTARED™ Enhanced Chemifluorescent Substrate having an excitation maximum at about 570 nm and an emission maximum at about 585 nm, etc.

In embodiments, analysis may be performed using a novel lab-on-chip utilizing wavelength backscattering with at least two wavelengths of light. For example, a light source 532 capable of emitting at least two wavelengths of light, such as a plurality of light emitting diodes, laser diodes, or other lasers, or a tunable laser, may be used to illuminate the washed sample 522, exciting the fluorophore 518 and causing light emission 530. The emission spectrum of the light emitted 530 from the fluorophore 518 may be optically sensed 534 and analyzed by, for example, an optical sensing "box" or circuit 536. Optical sensing circuit 536 may perform wavelength and amplitude analysis on the emitted light 530 and may determine the absence, presence, and/or quantity and isotype of antibody in the sample 522. In embodiments, such determination may be made in optical sensing circuit 536 and communicated to a computing device 538, such as a smartphone, tablet computer, laptop computer, personal computer, workstation computer, cloud computing service, etc. In embodiments, optical sensing circuit 536 may generate data representing the performed wavelength and amplitude analysis and may transmit that data to a computing device 538, such as a smartphone, tablet computer, laptop computer, personal computer, workstation computer, cloud computing service, etc., for determination of the absence, presence, and/or quantity of antibody in the sample 522.

In embodiments, no interpretation of results is needed by the user. The response may be given by a green, yellow, or red indicator per antibody isotype. Green may indicate a positive result, meaning the antibody has been detected against SARS-CoV-2, representing current or past infection by SARS-CoV-2 and an active immune response. An indeterminate or inconclusive result may be shown with a yellow indicator, which is likely due to user error or device malfunction. Red may indicate a negative result, meaning no immune response to SARS-CoV-2 was detected.

In embodiments, the testing device may be a self-contained device that does not require a laboratory for interpretation of results. In embodiments, the positive and negative controls may either be included with the device for consumer use or may be directly built into the self-contained device. For example, a separate channel with magnetic particles labeled with a fluorescent molecule can act as an internal control, which will be directly built into the disposable testing cartridge.

Because each testing cartridge is a single use device, representative cartridges from a given batch may be tested with positive or negative controls and if these are found to be valid and acceptable, other cartridges in the batch may be used. This process can be performed periodically to confirm the validity of the devices in the same batch. The testing device itself may be tested using special-purpose cartridges. Different types of cartridges may have different authentication chips embedded in them, allowing the device to work in "live" or "testing" mode as required. Such authentication chips may include authentication circuitry, identification circuitry, data storage circuitry, etc., and may identify the type of chip, the type of testing being performed, the patient being tested, etc.

Figure 7A:
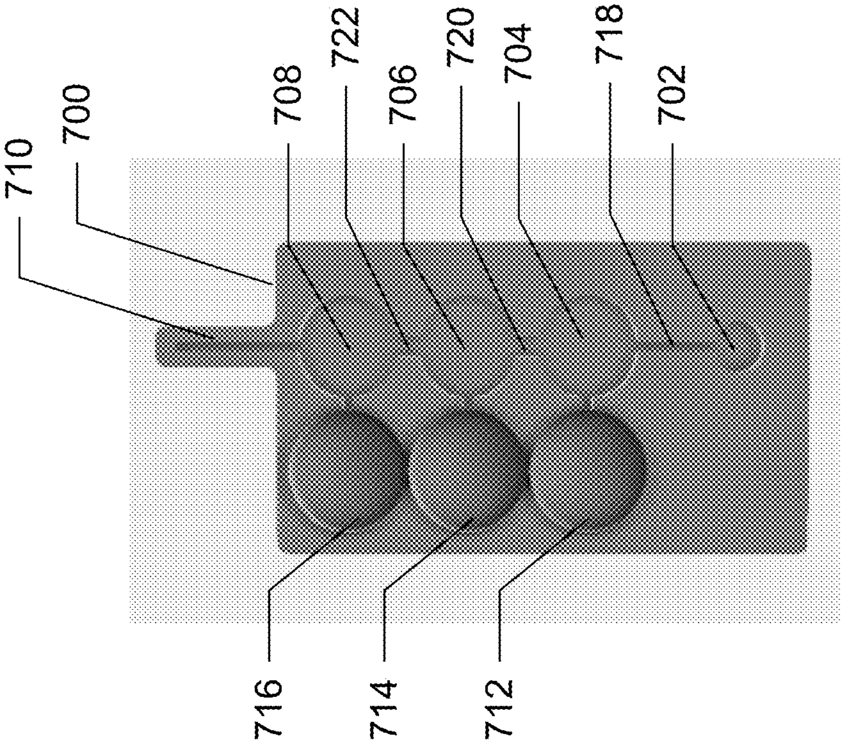
FIG. 7*a* is an exemplary top view of sample test cartridge according to embodiments of the present techniques.
Figure 7B:
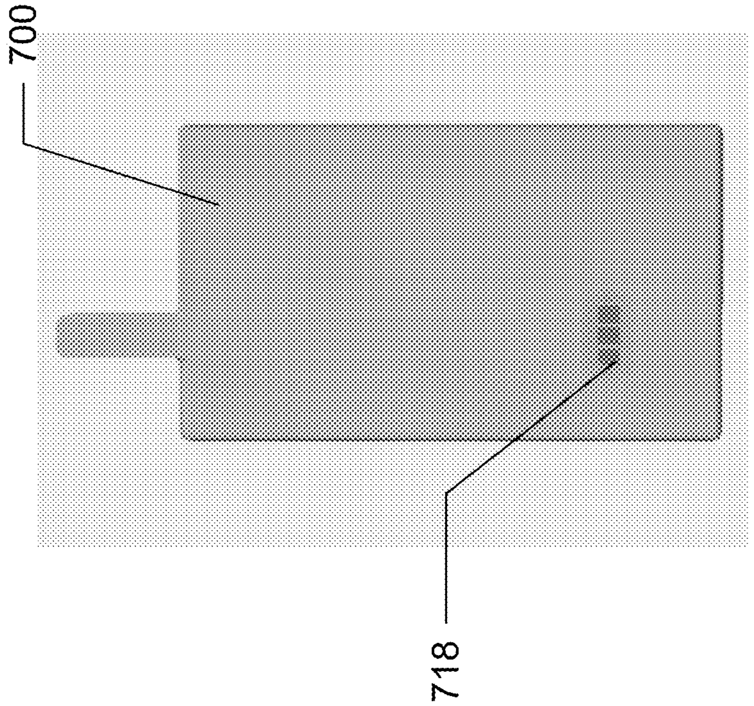
FIG. 7*b* is an exemplary bottom view of sample test cartridge according to embodiments of the present techniques.

An example of a test cartridge 700 is shown in FIGS. 7*a* and 7*b*. An exemplary top view of sample test cartridge 700 is shown in FIG. 7*a*. In this example, test cartridge 700 may include inlet port 702, mixer chamber 704, wash chamber 706, optional amplification chamber 708, mixer reservoir 712, wash reservoir 714, and optional amplification reservoir 716. Reservoirs 712, 714, and 716 may contain solvents, reagents, buffers, etc., in hermitically sealed blisters for storage. Mixer reservoir 712 may be pre-filled with the necessary reagent solvent and micromagnetic beads or particles having antigens to antibodies raised against SARS-CoV-2 immobilized on the particles. Wash reservoir 1004 1005 may be pre-filled with buffer agent. Optional amplification reservoir 716 may be prefilled with enzymatic amplification agents or buffer. Test cartridge 700 may also include a plurality of passages, such as passage 718 between inlet port 702 and chamber 704, passage 720 between chamber 704 and chamber 706, and passage 722 between chamber 706 and chamber 708.

Figure 6:
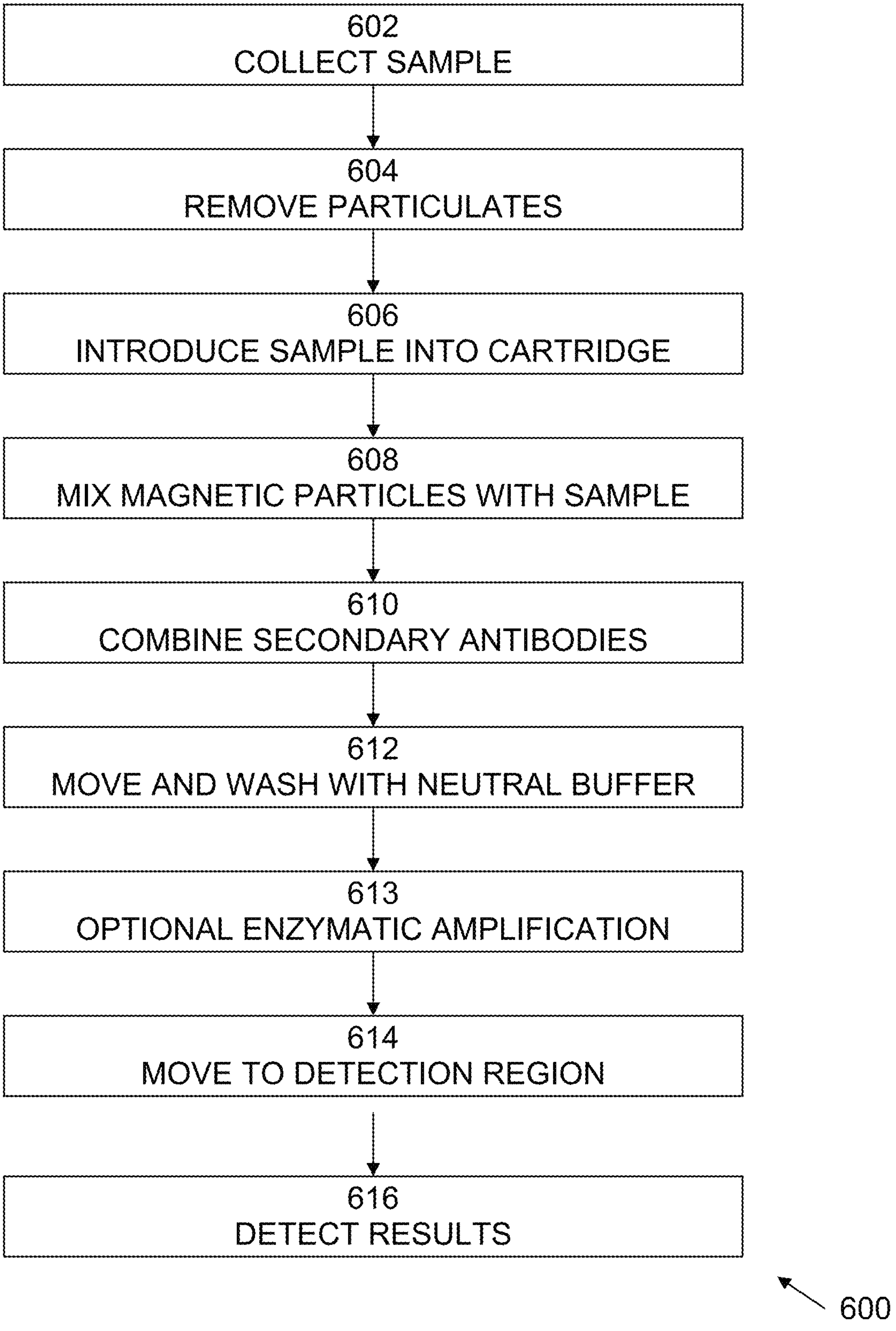
FIG. 6 is an exemplary flow diagram of a testing process according to embodiments of the present techniques.

In operation, the testing device may process test cartridge 702, for example, as described in conjunction with FIG. 6. Process 600 begins with 602, in which a saliva sample may be collected. At 606, a portion of saliva sample may be introduced into via inlet port 702 into chamber 704. At 608, cartridge 700 may be inserted into the device, and magnetic particles or beads in chamber 704 may be mixed with the sample. The magnetic particles may have one or more antigens to antibodies raised against SARS-CoV-2 immobilized on the particles. Antibodies present in the sample will bind to the antigens immobilized onto magnetic particles. Mixing may be facilitated by movement of the magnetic particles. The magnetic particles may be moved by application of electric current by testing device circuitry to magnetic coils or by movement of a magnetic field produced by magnetic coils or by a permanent magnet relative to cartridge 700, as described below.

At 610, a reagent solvent in chamber 712, including secondary antibodies (such as IgA, IgM, and IgG) labeled with a fluorescent compound, such as fluorescein, QUANTABLU™, QUANTARED™, etc., may be combined with the magnetic particles and mixed in chamber 704 to detect captured antibodies from the sample. At 612, the magnetic particles with attached IgA, IgM, and IgG and fluorescent compound may be moved to a washing station in chamber 706, and washed using a neutral buffer from chamber 714. At 613, the magnetic particles may optionally be moved into optional enzymatic amplification chamber 708 and optionally mixed with enzymatic amplification agents or buffer from optional amplification reservoir 716. At 614, the magnetic particles may be moved to a detection region in chamber 710 to obtain the signal from the fluorescent compound labelling the secondary antibodies 516 on the magnetic particles. Antibody isotypes may be distinguished using the color or light emission spectrum of fluorescent compound attached to the secondary antibody.

An exemplary bottom view of test cartridge 700 is shown in FIG. 7*b*. In this example, test cartridge 700 may include Authentication Chip 718.

Figure 8:
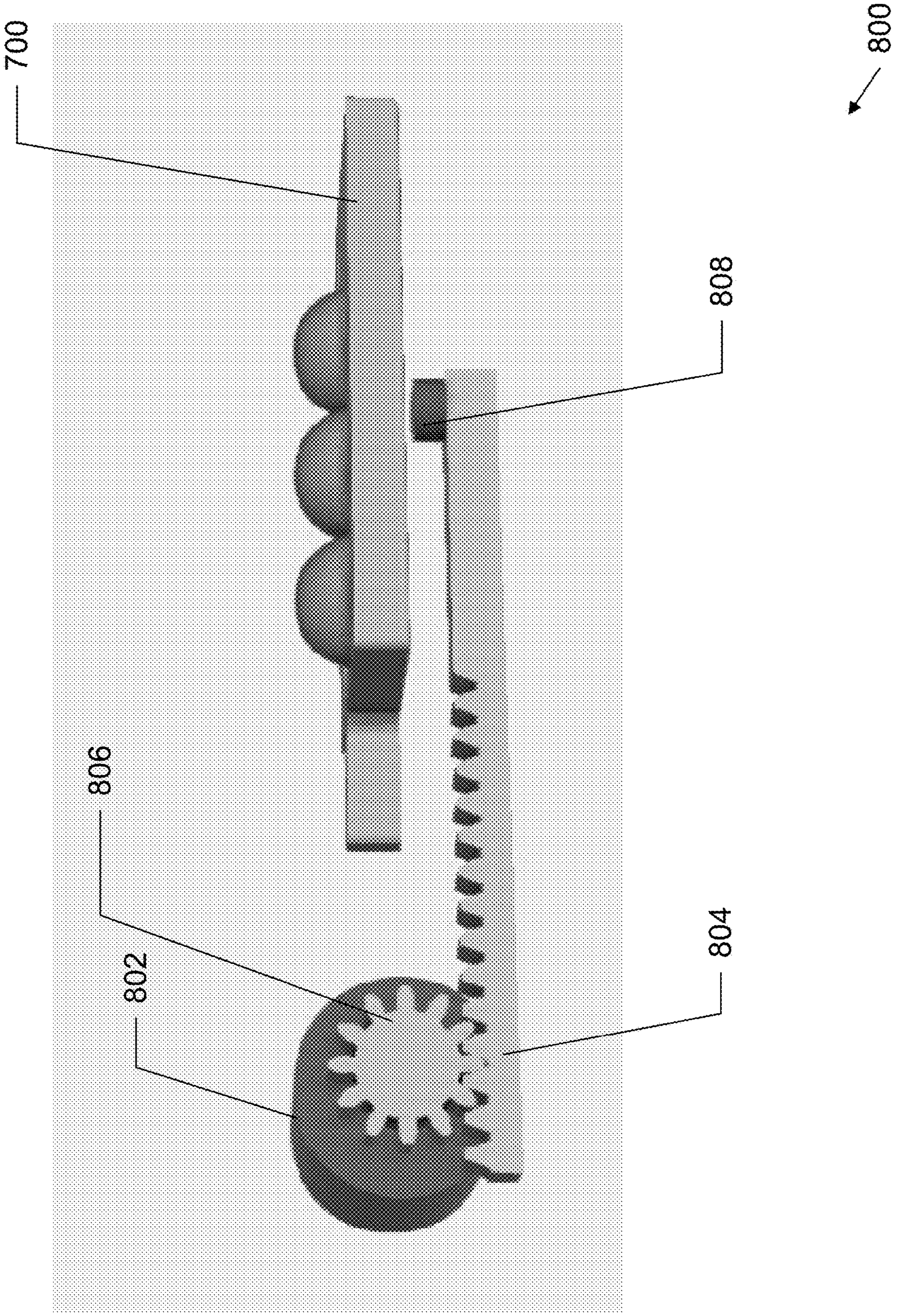
FIG. 8 is an exemplary illustration of a cartridge movement apparatus according to embodiments of the present techniques.

An exemplary cartridge movement apparatus 800, for performing reagent washing and mixing is shown in FIG. 8. In this example, apparatus 800 may include a servo motor 802, a rack 804 and pinion 806 gear mechanism, and a permanent magnet 808. Servo motor 802 may be controlled by control circuitry, as described below, and may turn pinion gear 806, causing movement of rack 804 and thus, movement of permanent magnet 808, which is attached to rack 804. Movement of permanent magnet 808 may be used to move the magnetic particles in cartridge 700. Permanent magnet 808 may, for example, be a neodymium alloy magnet. Using rack and pinion mechanism to move micromagnetic beads inside the cartridge to provide manipulation and movement of micromagnetic beads to achieve mixing and washing actions inside the cartridge reservoirs and for transporting the "washed" micromagnetic beads to the detection reservoir.

Figure 9:
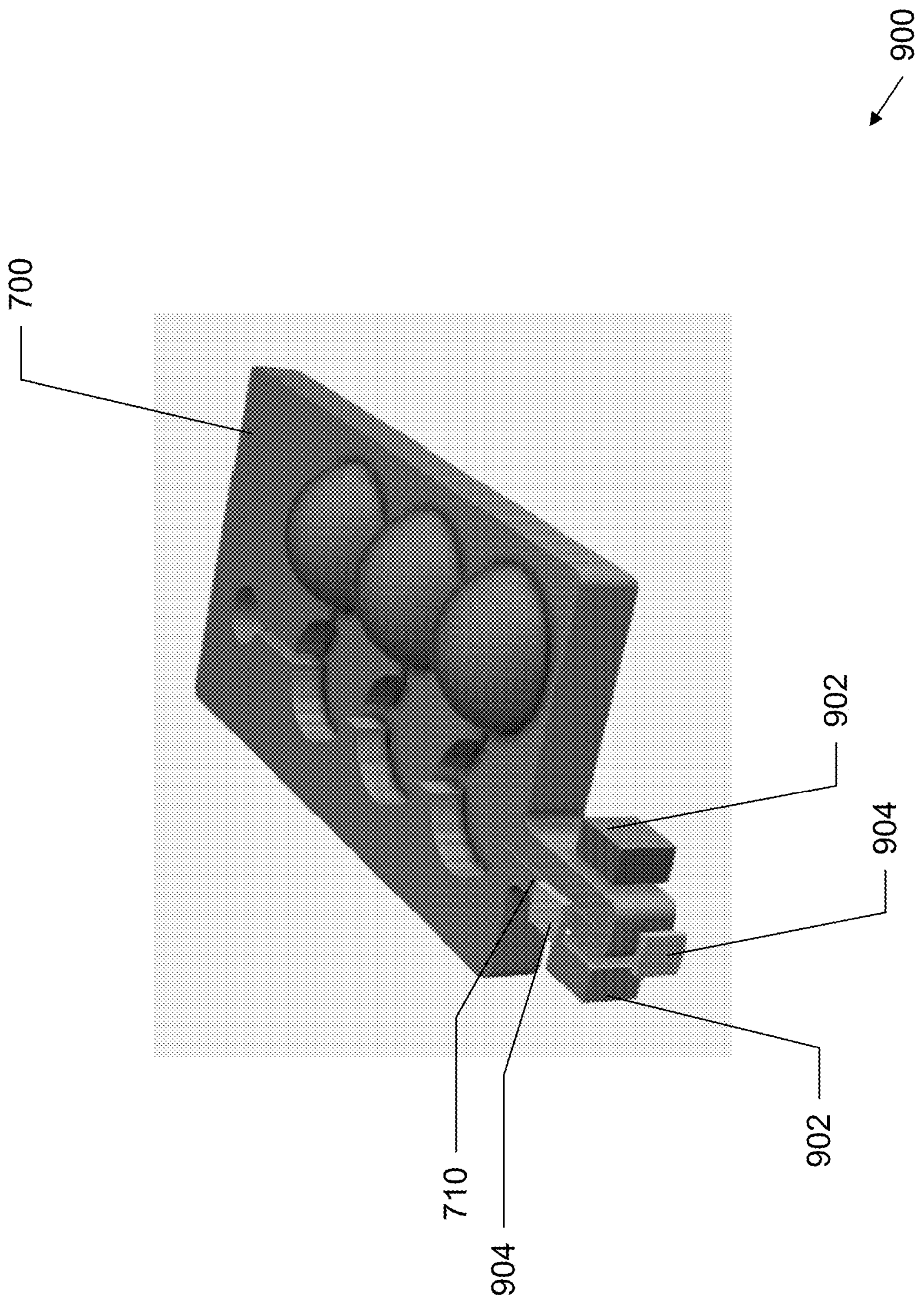
FIG. 9 is an exemplary illustration of an embodiment of fluorescence detection according to embodiments of the present techniques.

An exemplary embodiment of fluorescence detection apparatus 900 is shown in FIG. 9. As shown in this example, Multispectral photodiode chips 902 and excitation LEDs 904 may be arranged adjacent to the detection region in chamber 710, which contains the washed magnetic particles with attached IgA, IgM, and IgG and fluorescent compound. Excitation LEDs 904, as controlled by control circuitry, as described below, may illuminate the contents of chamber 710, causing excitation of fluorescent compounds and emission of light from the fluorescent compounds. Multispectral photodiode chips 902 may receive and detect the emission spectrum of light emitted from the fluorescent compounds, which may be analyzed, for example, by optical sensing circuitry and/or computing devices, as described herein, to determine the presence or absence of COVID-19 infection, antibodies, etc.

An exemplary block diagram of a test cartridge 1000 is shown in FIG. 10. In this example, test cartridge 1000 is a disposable sample cartridge made, for example, from clear glass or silica, transparent acrylic, other plastic, or other transparent material. Cartridge 1000 may include mixer chamber 1002, mixer reservoir 1003, wash chamber 1004, wash reservoir 1005, optional amplification chamber 1006, optional amplification reservoir 1007, detection reservoir 1010, and authentication chip 1008. Reservoirs 1003, 1005, and 1007 may contain solvents, reagents, buffers, etc., in hermetically sealed blisters for storage. Mixer reservoir 1003 may be pre-filled with the necessary reagent solvent and micromagnetic beads or particles having antigens to antibodies raised against SARS-CoV-2 immobilized on the particles. A patient saliva sample may be introduced into mixer chamber 1002 during testing and the reagent solvent and micromagnetic beads may be moved to mixer chamber 1002. Antibodies present in the sample will bind to the antigens immobilized onto magnetic particles. Mixing may be facilitated by movement of the magnetic particles. The magnetic particles may be moved by application of electric current by testing device circuitry to magnetic coils or by movement of cartridge 1000 relative to a magnetic field produced by magnetic coils or by a permanent magnet.

Wash reservoir 1005 may be pre-filled with buffer agent. Micromagnetic beads may be magnetically transported from mixer chamber 1002 to wash chamber 1004, and buffer agent may be moved to wash chamber 1004. In wash chamber 1004, the micromagnetic beads may be "cleaned" to ensure only bound analytes are detected. Optional amplification reservoir 1007 may be prefilled with enzymatic amplification agents or buffer. Micromagnetic beads may be magnetically transported from wash chamber 1004 to amplification chamber 1006, and enzymatic amplification agents or buffer may be moved to amplification chamber 1006. In amplification chamber 1006, optional enzymatic amplification may be performed. Detection reservoir 1010 may be pre-filled with buffer agent. Micromagnetic beads may be magnetically transported from wash reservoir 1004 or optional amplification chamber 1006 to detection reservoir

1010, where, for infected patients, fluorescence from micro-magnetic beads may be detected by way of illuminating LEDs and multi-spectrum photodiodes, as described herein.

Figure 11:
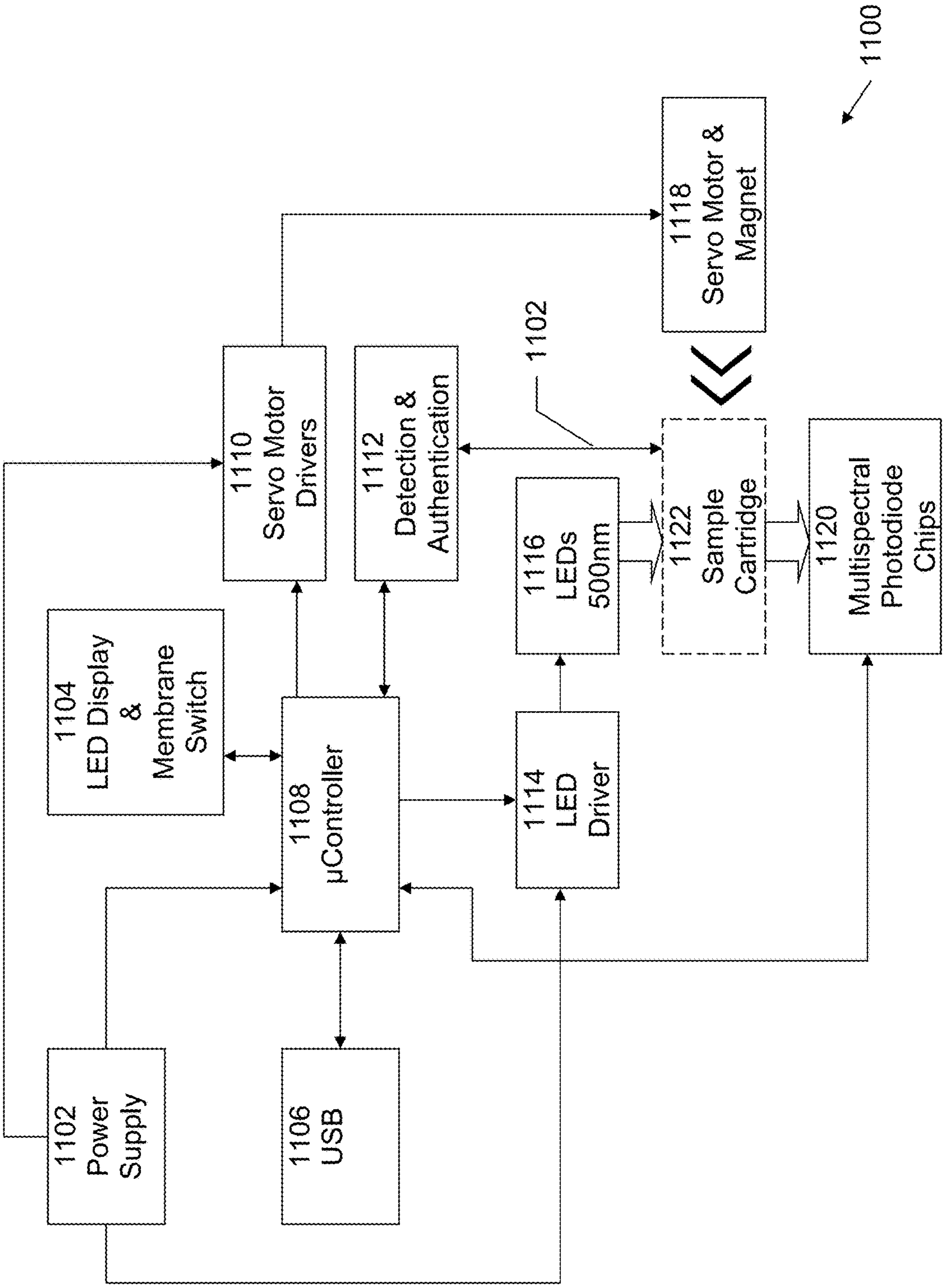
FIG. 11 is an exemplary block diagram of a testing device according to embodiments of the present techniques.

An exemplary block diagram of a testing device 1100 is shown in FIG. 11. In this example, testing device 1100 may include power supply 1102, user interface 1104, such as an LED display and membrane switch buttons, communication interface 1106, such as a USB port or wireless communications adapter, microcontroller 1108, servo motor drivers 1110, detection and authentication circuitry 1112, LED driver 1114, sample excitation LEDs 1116, servo motor, rack and pinion, and magnet assembly 1118, light detector 1120, and insertable sample cartridge(s) 1122. Power supply 1102 may provide electrical power to the other components of testing device 1100 and may include batteries or other electrical and electronic components, such as voltage regulators to provide different voltage supply levels as needed. User interface 1104, may include, for example, an LED display and membrane switch buttons, or other display and/or input/output devices. Embodiments may include other configurations of front panel, as well as other display devices, such as LCD displays, numeric displays, etc., which may display additional information, such as concentration, amount, percentage, etc., of antibodies, fluorescent indicator, threshold levels, etc.

Communication interface 1106, may include, for example a USB port or wireless communications adapter, such as Wi-Fi, Bluetooth, cellular data, or other wireless communications technique. Microcontroller 1108 may include one or more processors, memory, input/output circuitry, and other circuitry to control the operation of testing device 1100 and to provide interfacing to external computers for data transfer of information including test results, patient information, etc., via USB port or wireless communications adapter and to provide interfacing to the authentication chip on the sample cartridge. Servo motor drivers 1110 may include electronic circuitry to provide electrical current to drive the operation of servo motor 1118 as controlled by microcontroller 1108. Detection and authentication circuitry 1112 may include circuitry to interface microcontroller 1108 with authentication chip 718, 1008, shown in FIGS. 7 and 10. Such authentication chips may include authentication circuitry, identification circuitry, data storage circuitry, etc., and may identify the type of chip, the type of testing being performed, the patient being tested, etc. Detection and authentication circuitry 1112 may allow microcontroller 1108 to access this information, allowing configuration of testing device 1100 based thereupon, for example, allowing the device to work in "live" or "testing" mode as required.

LED driver 1114 may include electronic circuitry to provide electrical current to drive the operation of sample excitation LEDs 1116, as controlled by microcontroller 1108. Sample excitation LEDs 1116 may provide light to excite the fluorescent compounds in the sample under test, as described herein. For example, sample excitation LEDs may emit light for excitation of fluorescent compounds at 500 nm wavelength, or other suitable wavelength for excitation of the fluorescent compounds. Multiple LEDs may be provided to increase the intensity, as well as to achieve a more uniform illumination of the sample. Servo motor, rack and pinion, and magnet assembly 1118 may include, for example, the apparatus shown in FIG. 8, and described in reference thereto. Light detector 1120 may include electronic circuitry to detect light emitted by the excited fluorescent compounds in the sample under test, as described herein. Light detector 1120 may, for example, include multispectral photodiodes chips, such as the AMS® multi-channel AS7265x chipset, or other suitable light detectors. Sample cartridge 1120 may include, for example, a test cartridge 700 similar to that shown in FIGS. 7*a*, 7*b*, 9, 10, etc.

Figure 12B:
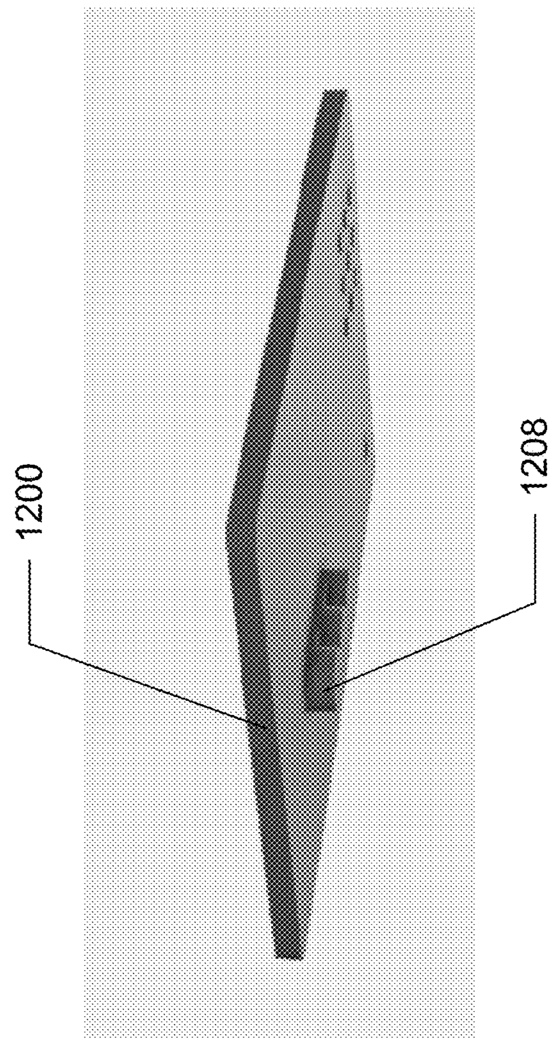
FIG. 12*b* is an exemplary illustration of a front panel of a testing device according to embodiments of the present techniques.
Figure 12A:
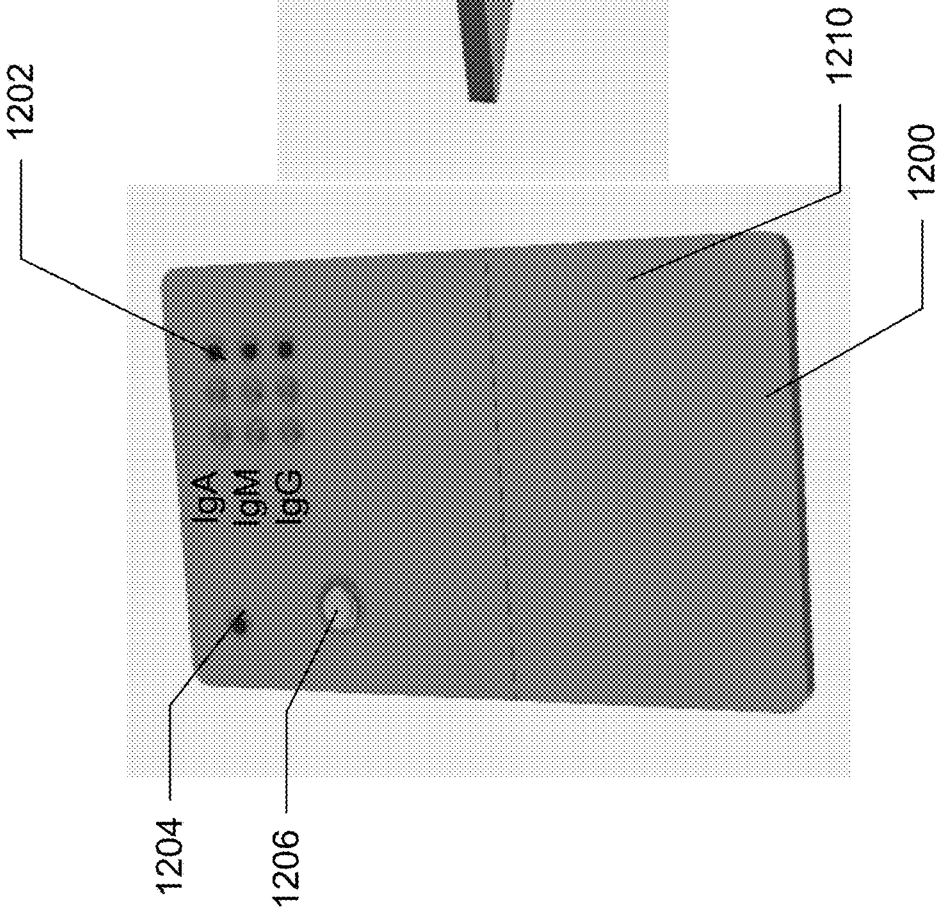
FIG. 12*a* is an exemplary illustration of a front panel of a testing device according to embodiments of the present techniques.
Figures 3, 16:
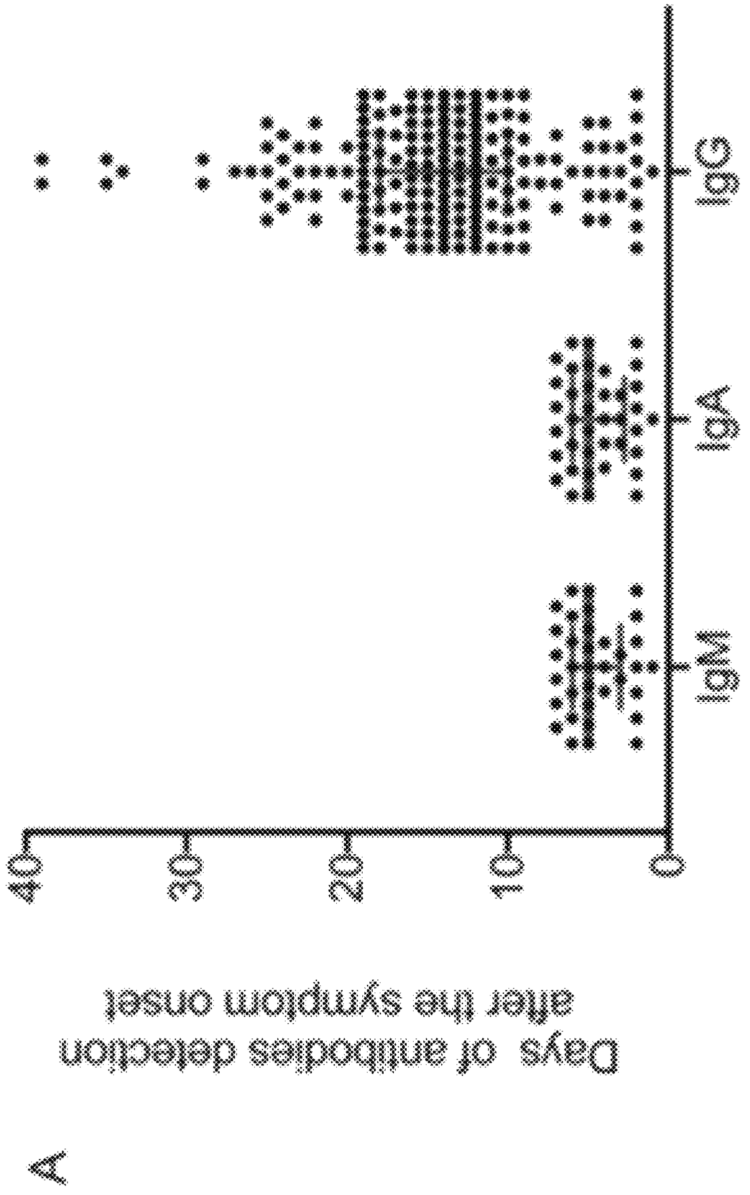
FIG. 16 is an exemplary block illustration of antibody types present at different stages of disease, as may be utilized by embodiments of the present techniques.

An exemplary front view of a front panel 1200 of testing device 1100 is shown in FIG. 12*a*. In this example, front panel 1200 may include test result indicators 1202, test in progress indicator 1204, and operation switch 1206. In this example, test result indicators 1202 may include three by three LEDs (red, yellow, green) to provide intuitive test result based on predetermined threshold levels for IgA, IgM, and IgG. In embodiments, only one color (green, yellow, or red) will result for each antibody. For example, a green light may indicate the user sample is positive for the respective antibody, a red light may indicate the user does not have the respective antibody in high enough quantities to be detected by the device, a yellow light may indicate an indeterminate result. Research may show (for example, see FIG. 16 and Table 1) that IgA and IgM are produced and persist in early stages of the disease (Days 0-14), and IgG is produced starting on Day 0 of the disease and levels plateau after Day 20 (Guo, et al., 2020).

TABLE 1

| | |
|---|---|
| IgA | early stage |
| IgM | early stage |
| IgA + IgM | early stage |
| IgA + IgG | early stage |
| IgM + IgG | early stage |
| IgA + IgM + IgG | early stage |
| IgG | late stage |

This may roughly imply that a positive for IgA or IgM means the patient is in early stages of infection, and the presence of IgG alone means the patient is in later stages of infection. Thus, embodiments may detect which of the patients has a mounted immune response to the virus. As the test will be able to detect which antibodies bind to the spike protein, which is the protein that binds to the ACE receptors in the lungs to cause infection, this test may be able to detect which patients have raise neutralizing antibodies toward the virus.

Returning to FIG. 12*a*, test in progress indicator 1204 may include a status LED indicating the test in progress. Operation switch 1206 may include a membrane switch for an operator to start the test process. Embodiments may include other configurations of front panel, as well as other display devices, such as LCD displays, numeric displays, etc., which may display additional information, such as concentration, amount, percentage, etc., of antibodies, fluorescent indicator, threshold levels, etc.

An exemplary rear view of a front panel 1200 of testing device 1100 is shown in FIG. 12*b*. In this example, front panel 1200 may include a plurality of spring-backed actuators 1208 in a closable door portion 1210 of front panel 1200 to apply pressure, when the door is closed, to the reservoir blisters and move the reagents, solvents, and buffers, etc. into their associated chambers.

Figure 13B:
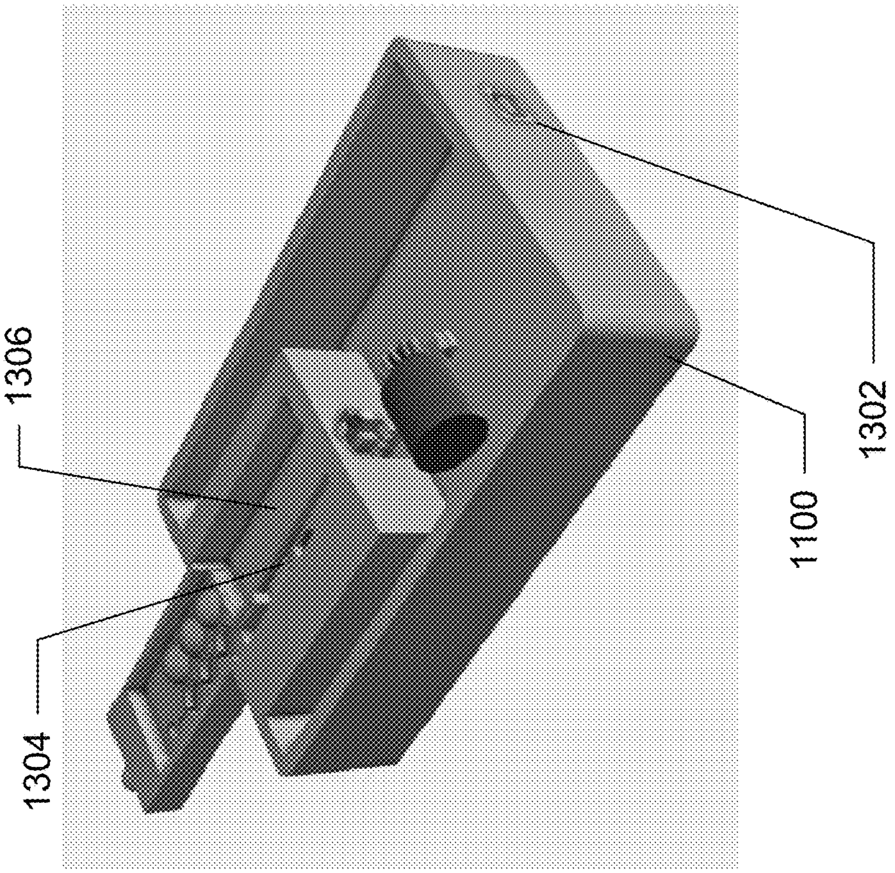
FIG. 13*b* is an exemplary internal view of a testing device according to embodiments of the present techniques.
Figure 13A:
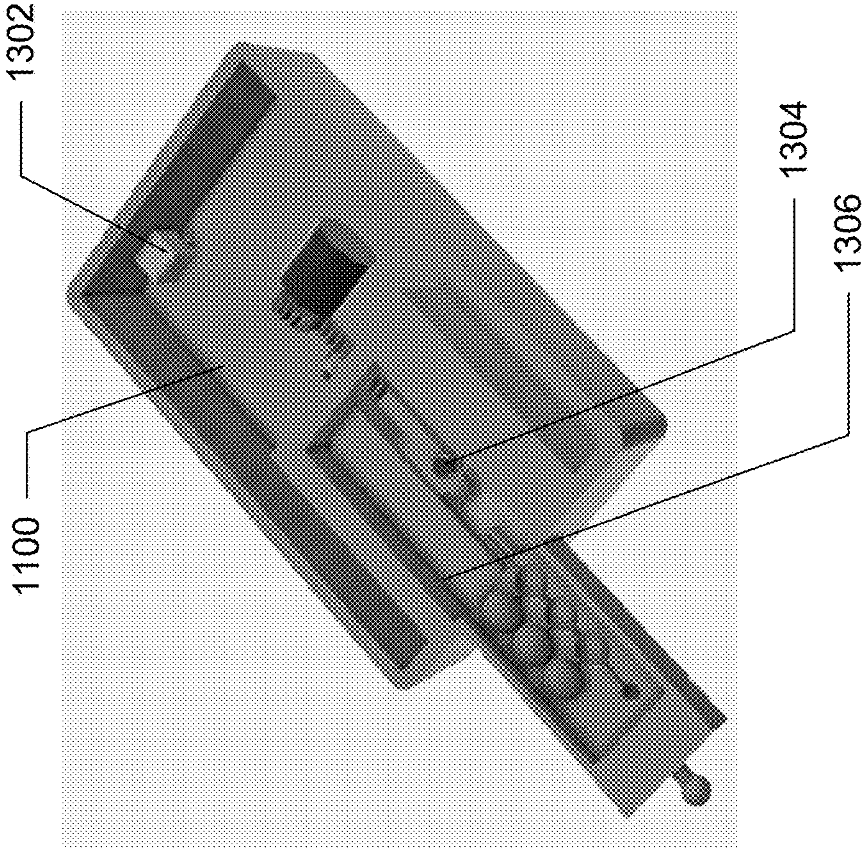
FIG. 13*a* is an exemplary internal view of a testing device according to embodiments of the present techniques.

An exemplary internal view of testing device 1100 is shown in FIGS. 13*a* and 13*b*. In this example, USB-B connector 1302, authentication chip reader connector 1304, and cartridge holder tray 1306 are shown.

Figure 17:
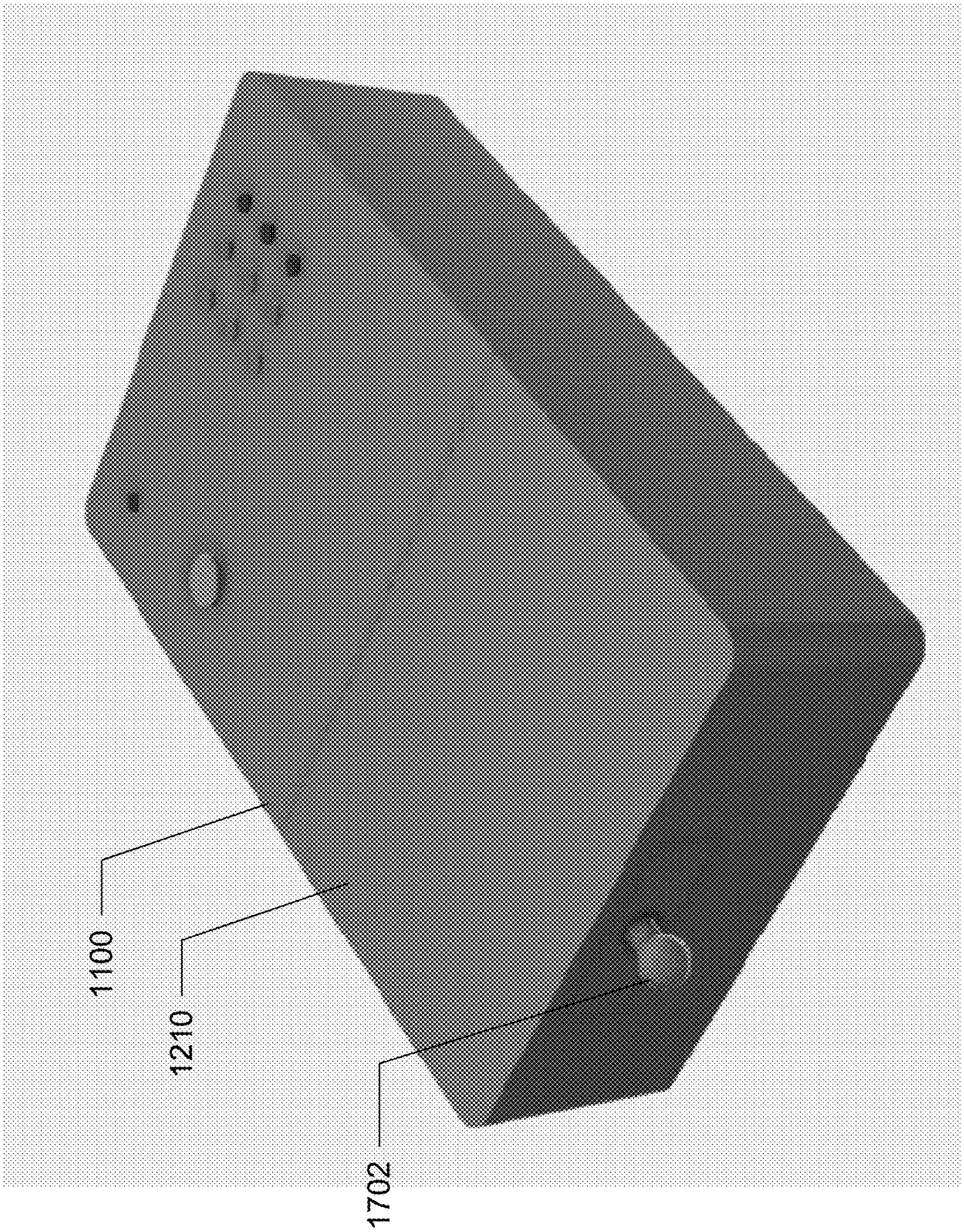
FIG. 17 is an exemplary internal view of a testing device according to embodiments of the present techniques.

An exemplary external view of testing device 1100 is shown in FIG. 17. In this example, after a sample cartridge is inserted into testing device 1100, door 1210 may be closed and a latch 1702 may be activated, preventing removal of the cartridge during the test. When door 1210 is closed, spring-backed actuators 1208, shown in FIG. 12*b*, may apply pressure to the reservoir blisters and move the reagents, solvents, and buffers, etc. into their associated chambers.

Figure 14:
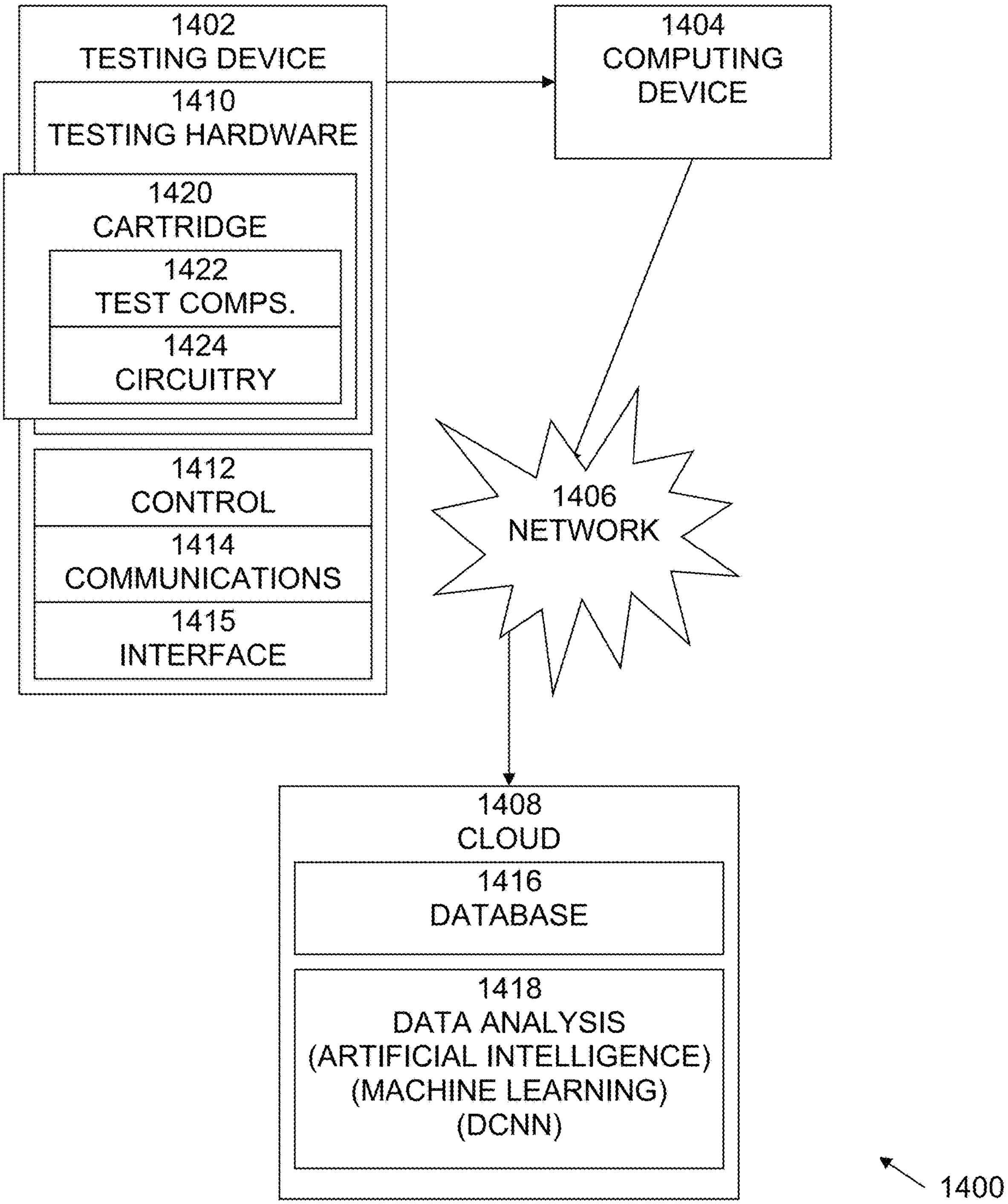
FIG. 14 is an exemplary block diagram of a testing system according to embodiments of the present techniques.

An exemplary testing system 1400 is shown in FIG. 14. System 1400 may include testing device 1402, computing device 1404, network 1406, and cloud computing system 1408. Testing device 1402 may be a stand-alone or integrated device and may include testing hardware 1410, control circuitry 1412, and communications circuitry 1414. Testing hardware 1410 may include the components shown in FIGS. 3, 4, and/or 5, as described above, and that performs the testing functions described above. Testing hardware 1410 may include components to interface with an inserted test cartridge 1420, which may include test components 1422, such as a microfluidic silica chip with etched capillaries and chambers, and circuitry 1424, which may include authentication circuitry, identification circuitry, data storage circuitry, etc. Testing hardware 1410 may further include components such as circuitry to apply, and to control the application of, electric current to magnetic coils that may be formed on cartridge 1420 or that may be present in the testing device 1402 and may be adjacent to or in the vicinity of cartridge 1420. Control circuitry 1412 may include control logic, controller, or processor circuitry to control performance of the physical, optical, electrical, and computing processes involved in operating testing device 1402, such as controlling the electric current in the magnetic coils, and in performing the functions described above. Communications circuitry 1414 may include circuitry to provide wired and/or wireless communications with one or more external or integrated devices, such as computing device 1404. In embodiments, testing device 1402 may also include interface 1415, which may include indicator or display components for direct display of test results from testing device 1402 and/or buttons, etc., for direct entry of information into testing device 1402.

Computing device 1404 may be an integrated or standalone device, such as a smartphone, tablet computer, laptop computer, personal computer, workstation computer, cloud computing service, etc., to communicate with testing device 1402. Computing device 1404 may provide processing and analysis of data received from testing device 1402, as well as communications with testing device 1402 and with cloud computing system 1408 vis network 1406. In embodiments, computing device 1404 may also include indicator or interface displays (not shown) for display of test results from testing device 1402 and/or entry of information into testing device 1402. Network 1406 may be any public or proprietary LAN or WAN, including, but not limited to the Internet, carrier network, wireless network, etc. Cloud computing system 1408 may provide on-demand availability of computer system resources, such as database storage 1416 and computing power/data analysis 1418, which is typically implemented in data centers available to many users over the Internet.

In embodiments, the optical analysis may result in imaging representative of sample 402. The resulting imaging, using machine learning techniques, may be used to detect protein structure geometry (Daaboul, G. G., et al. 2017). Then, combined inputs from chemical lab-on-chip sensors and the optical sensors, both included in testing hardware 1410 may be analyzed 1418, for example, using cloud computing system 1408, using both commonly available and proprietary Artificial Intelligence/Machine Learning (AI/ML) architectures, such as a Deep Cognitive Neural Network (DCNN), such as that described in U.S. Patent Application Publication No. 2019/0156189, published May 23, 2019, which is hereby incorporated by reference herein. Machine learning algorithms may be trained to detect the coronavirus family of viruses, and over time, using additional sample data, will become more effective at identifying different strains of the virus.

In embodiments, the machine algorithms may be further trained to detect other classes of viruses and specific strains of viruses or other pathogens, or trained for detection of neurodegenerative disease markers. The computing device 1404 computational platform may interface with a cloud computing platform 1408, opening up applications using anonymized patient and third party data.

Figure 15:
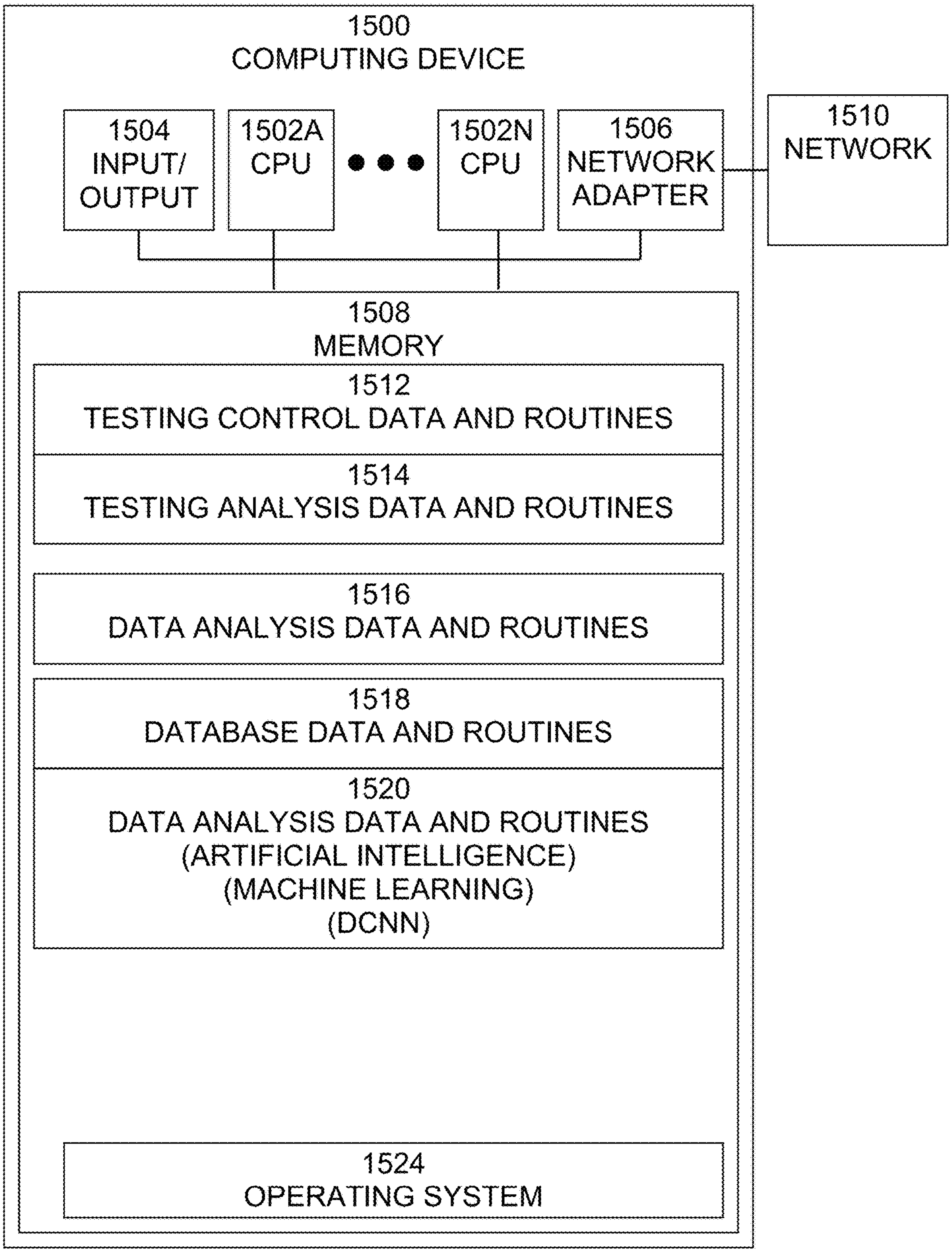
FIG. 15 is an exemplary block diagram of a computing device, in which processes involved in the embodiments described herein may be implemented.

An exemplary block diagram of a computing device 1500, in which processes involved in the embodiments described herein, such as computing device 1406 or cloud computing system 1408, may be implemented, is shown in FIG. 15. Computing device 1500 may be implemented using one or more programmed general-purpose computer systems, such as embedded processors, systems on a chip, personal computers, workstations, server systems, and minicomputers or mainframe computers, or in distributed, networked computing environments. Computing device 1500 may include one or more processors (CPUs) 1502A-1502N, input/output circuitry 1504, network adapter 1506, and memory 1508. CPUs 1502A-1502N execute program instructions in order to carry out the functions of the present communications systems and methods. Typically, CPUs 1502A-1502N are one or more microprocessors, such as an INTEL CORE® processor. FIG. 15 illustrates an embodiment in which computing device 1500 is implemented as a single multi-processor computer system, in which multiple processors 1502A-1502N share system resources, such as memory 1508, input/output circuitry 1504, and network adapter 1506. However, the present communications systems and methods also include embodiments in which computing device 1500 is implemented as a plurality of networked computer systems, which may be single-processor computer systems, multi-processor computer systems, or a mix thereof.

Input/output circuitry 1504 provides the capability to input data to, or output data from, computing device 1500. For example, input/output circuitry may include input devices, such as keyboards, mice, touchpads, trackballs, scanners, analog to digital converters, etc., output devices, such as video adapters, monitors, printers, etc., and input/output devices, such as, modems, etc. Network adapter 1506 interfaces device 1500 with a network 1510. Network 1510 may be any public or proprietary LAN or WAN, including, but not limited to the Internet.

Memory 1508 stores program instructions that are executed by, and data that are used and processed by, CPU 1502 to perform the functions of computing device 1500. Memory 1508 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 1508 may vary depending upon the function that computing device 1500 is programmed to perform. In the example shown in FIG. 15, exemplary memory contents are shown representing routines and data for embodiments of the processes described above. However, one of skill in the art would recognize that these routines, along with the memory contents related to those routines, may not be included on one system or device, but rather may be distributed among a plurality of systems or devices, based on well-known engineering considerations. The present systems and methods may include any and all such arrangements.

In the example shown in FIG. 15, memory 1508 may include, in the case of a testing device 1402, testing control data and routines 1512, testing analysis data and routines 1514, in the case of a computing device 1404, data analysis data and routines 1518, and in the case of a cloud computing system 1408, database data and routines 1520, and data analysis data and routines 1522 and operating system 1524. Testing control data and routines 1512 may include software routines to control performance of the physical, optical, electrical, and computing processes involved in operating testing device 1402, as well as data obtained from such testing, as described above. Testing analysis data and routines 1514 may include software routines to perform initial analysis and derivation of data obtained from testing, as described above. Data analysis data and routines 1514 may include, which may include software routines to perform processing and analysis of data received from testing device 1402, as described above. Authentication/matching routines 1514 may include modular proximity test routines 1518, which may include software routines to perform modular proximity testing on received authentication data, as described above. Database data and routines 1520, may include software routines to provide database storage of data on cloud computing system 1408, as described above. Data analysis data and routines 1522 may include software routines to provide computing power/data analysis on cloud computing system 1408, as described above. Operating system 1524 may provide overall system functionality.

As shown in FIG. 15, the present communications systems and methods may include implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multitasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments may employ an automated sandwich immunoassay method. The assay may be accomplished using affinity capture of antibodies through an immunoassay approach on magnetic beads, and the steps of the sandwich assay may be automated by moving the beads through the separate reservoirs using a magnet.

Figure 19:
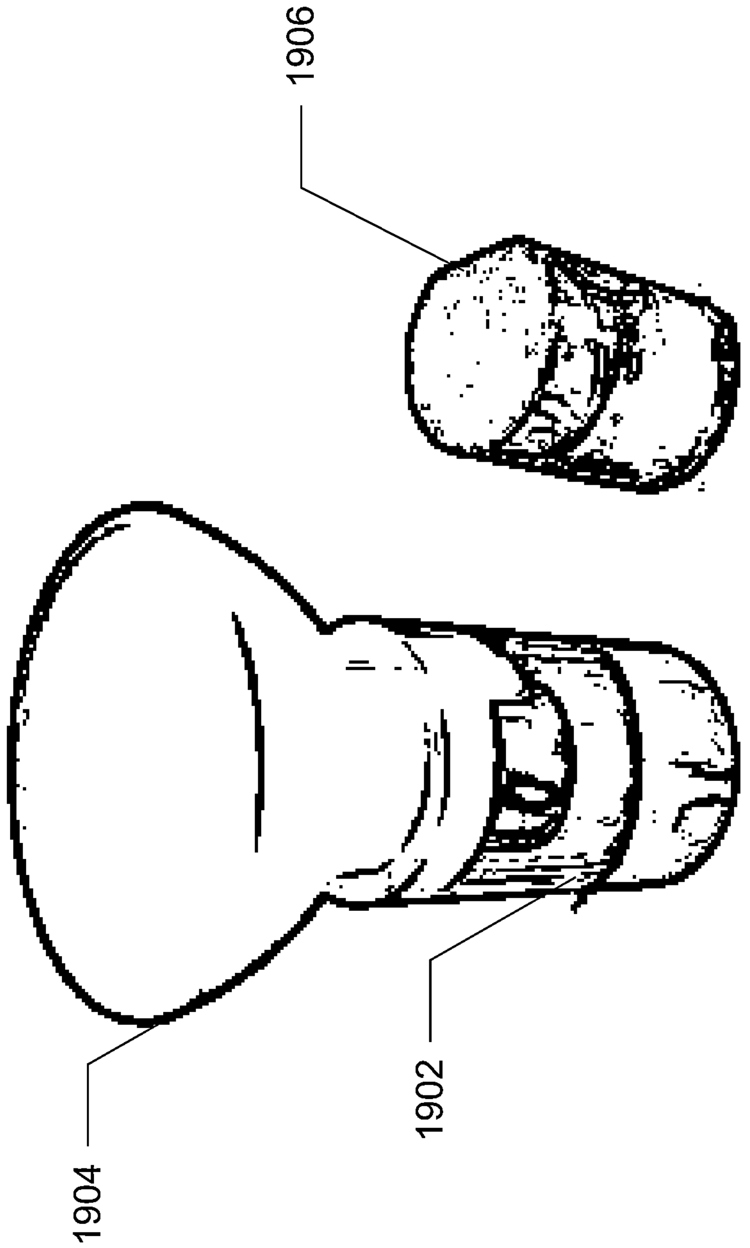
FIG. 19 is an exemplary illustration of an apparatus for test sample collection according to embodiments of the present techniques.
Figure 20:
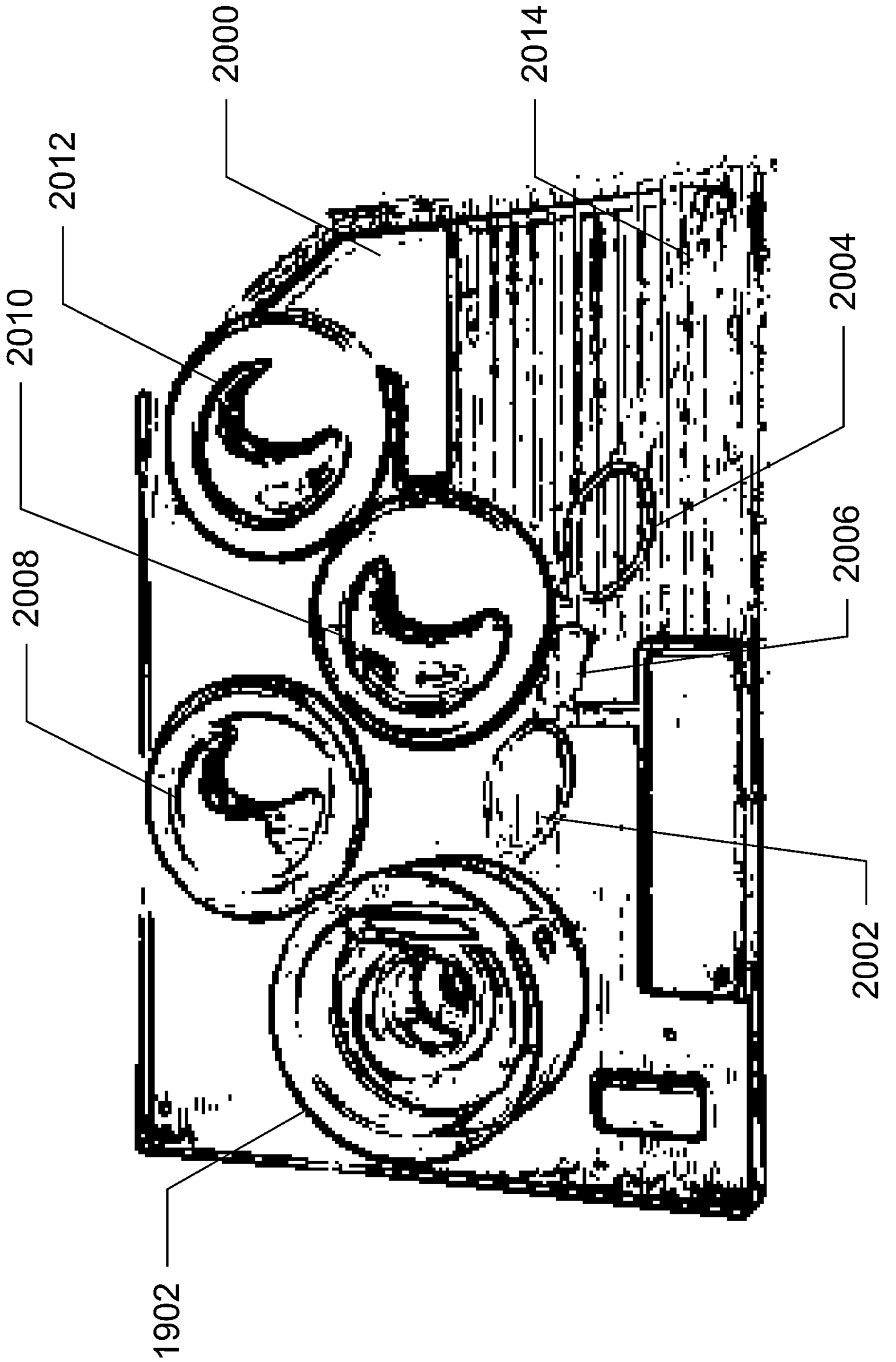
FIG. 20 is an exemplary illustration of a cartridge for test sample analysis according to embodiments of the present techniques.
Figure 21:
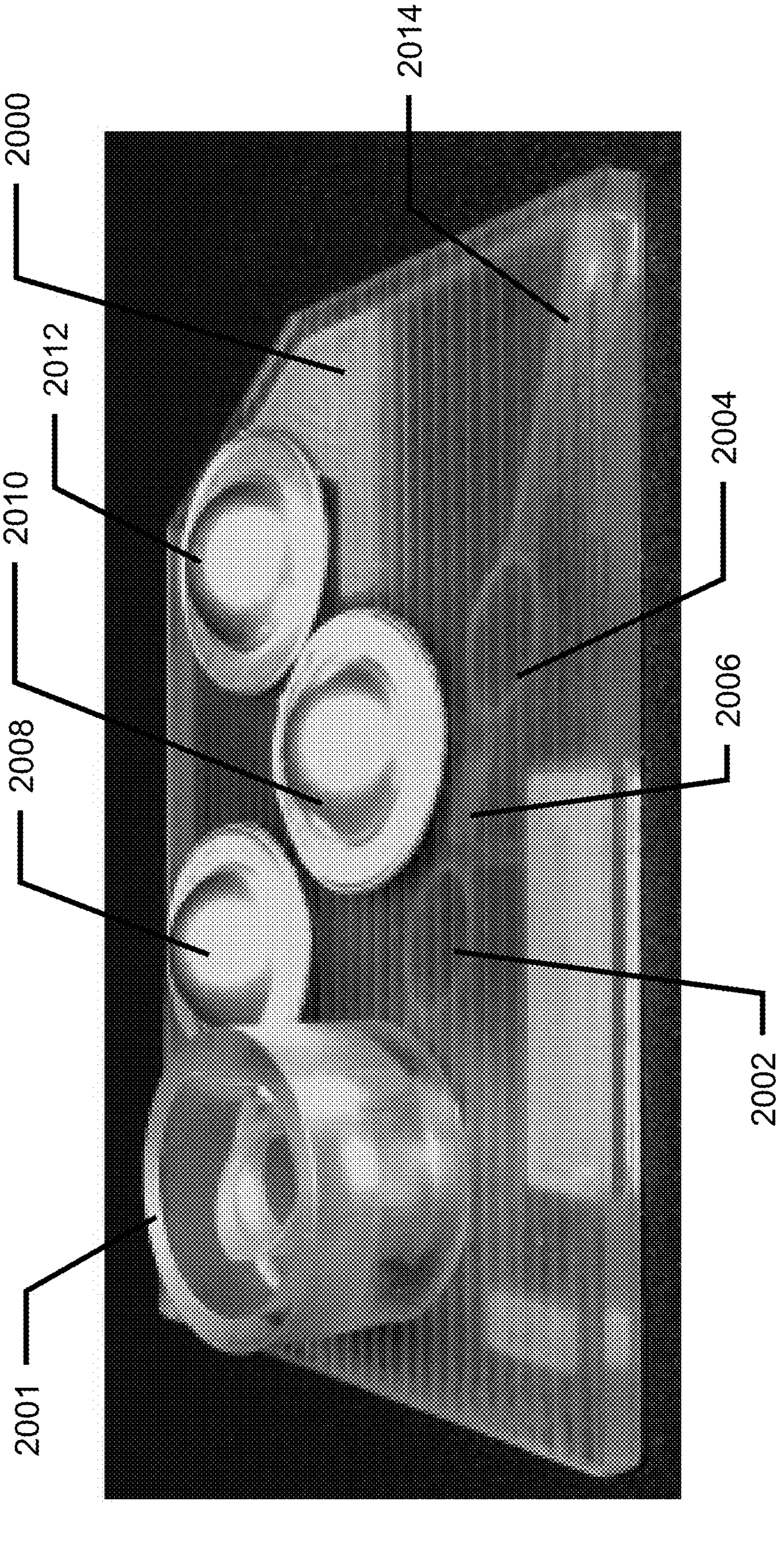
FIG. 21 is an exemplary illustration of a cartridge for test sample analysis according to embodiments of the present techniques.
Figure 23:
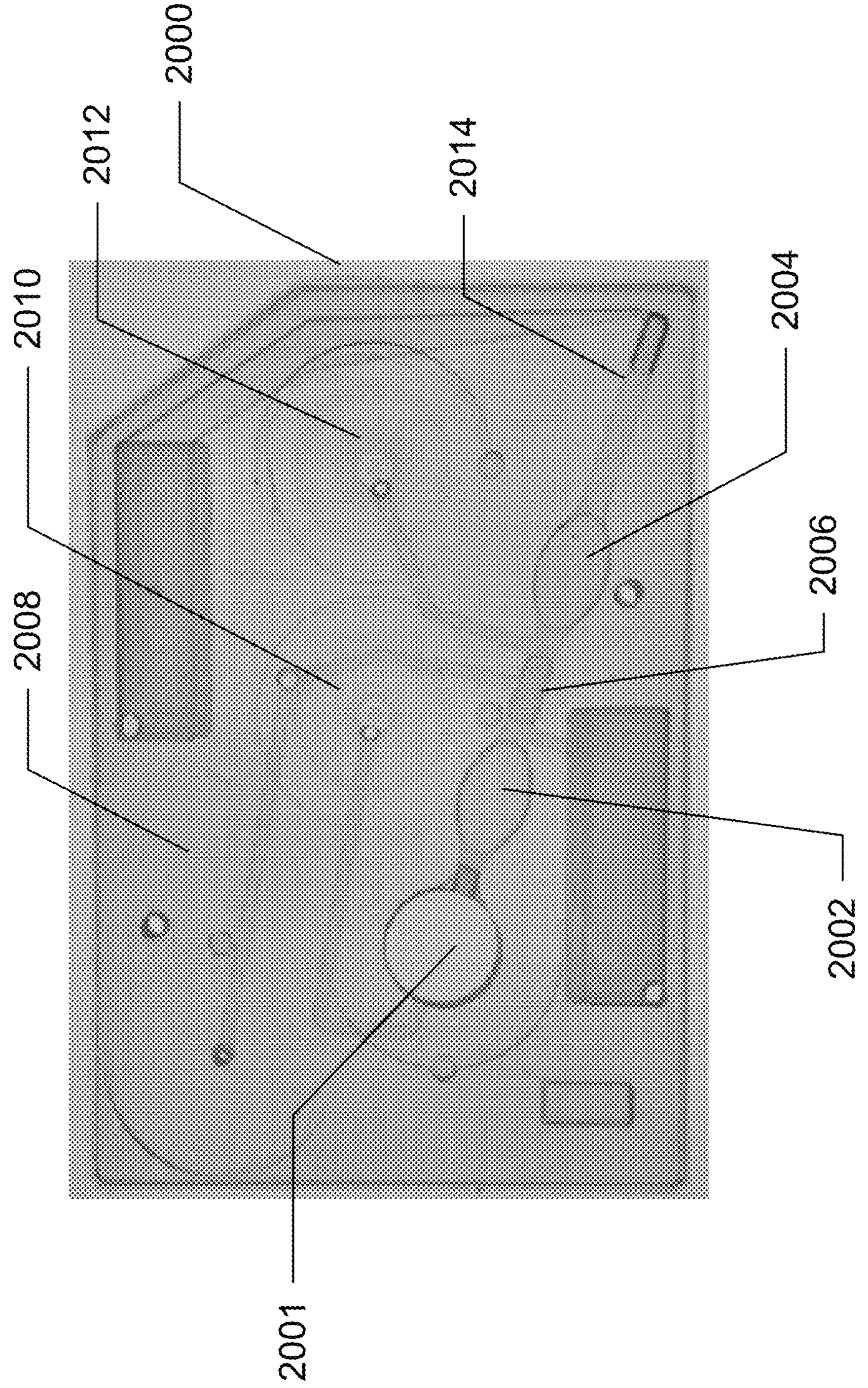
FIG. 23 is an exemplary illustration of a cartridge for test sample analysis according to embodiments of the present techniques.

For example, a test subject may provide a saliva sample of ≥0.2 mL by a passive drool method into a collection vial 1902, shown in FIG. 19, with an attachable funnel 1904. After collection, a cap containing reagents 1906 may be attached to the vial, bursting a foil cover in the process, and releasing magnetic particles and secondary antibodies into the sample. In a positive test, SARS-CoV-2 viral antigen, the S1 subunit of the spike membrane protein immobilized on the magnetic beads, will selectively bind to the SARS-CoV-2 antibodies present in the saliva sample and fluorescent-labeled secondary antibodies will attach to the captured antibodies, forming a sandwich immunocomplex.

Figure 24:
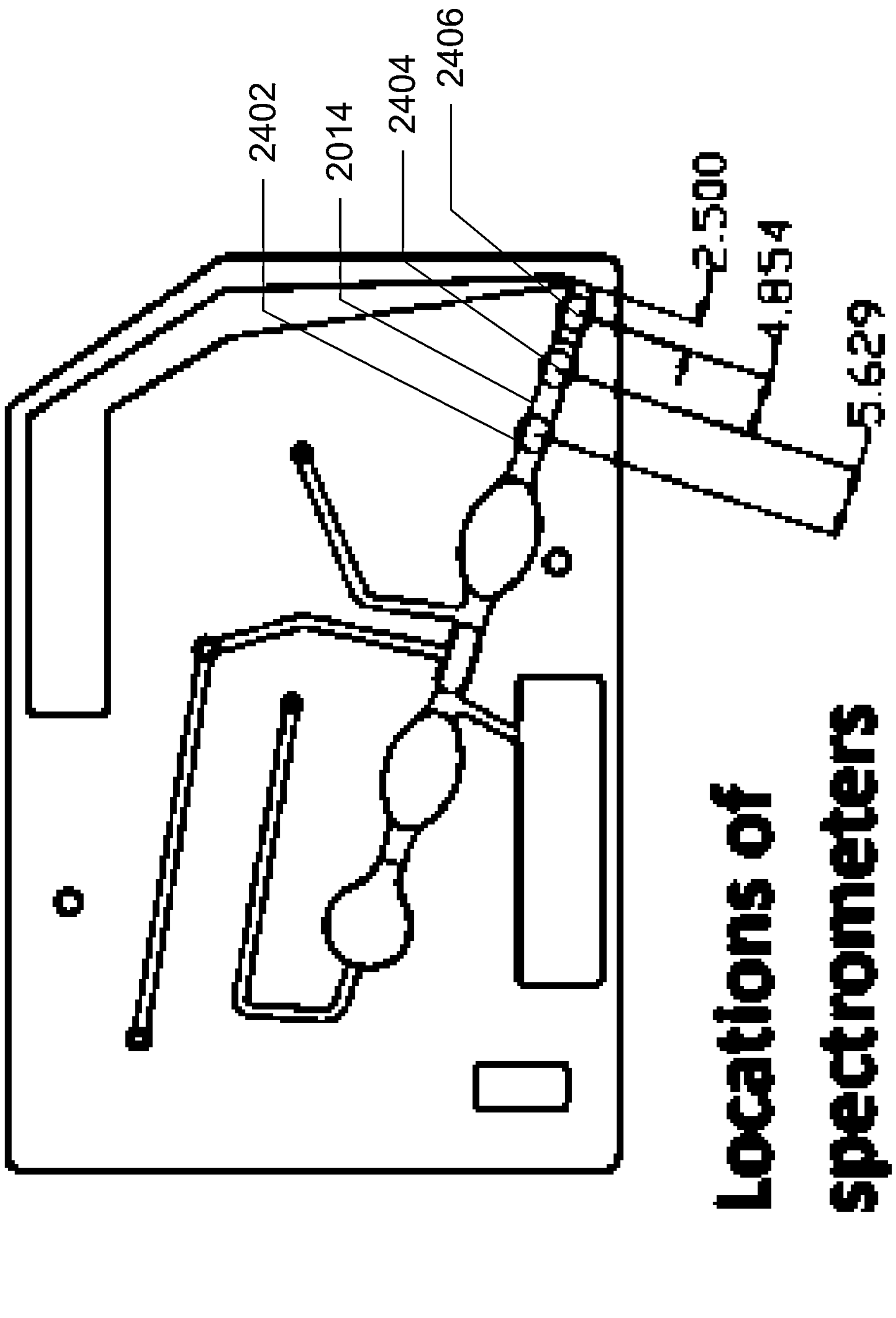
FIG. 24 is an exemplary illustration of a cartridge for test sample analysis according to embodiments of the present techniques.

After incubation with the reagents, as shown in FIGS. 20, 21, 23, and 24 the vial 1902 may be attached to port 2001 of a cartridge 2000 to be inserted into the analyzer device for analysis. The cartridge may include two low-volume reservoirs 2002, 2004 separated by a valve 2006, which are filled with buffer solution via blisters 2008, 2010, 2012. The magnetic beads containing the immunocomplex are transported in steps through each wash buffer reservoir 2002, 2004 in order to remove any components of the saliva sample that do not bind to the immobilized protein 2002, as well as excess secondary antibodies 2004. The washed magnetic beads may then be transported to detection region 2014, where the fluorescence of the fluorescent-labeled secondary antibodies may be excited and detected. For example, as shown in FIG. 24, spectrometers 2402, 2404, and 2406 may be located to detect the fluorescence of the fluorescent-labeled secondary antibodies, and thus, the presence of pathogens or antibodies to the pathogens in the sample.

Within the reagent cap 1906, four different types of fluorescent dye may be used, which have been selected to avoid overlap in their wavelength ranges, optimizing the precision of fluorescence readings for each labeled protein. One of the dyes may be conjugated to bovine serum albumin and immobilized on a portion of the beads contained in the reagent cap for use as an internal standard. The internal standard allows for precise calibration of the detector, and ensures that the analyzer is functioning properly during each test.

An exemplary flow diagram of reagent processing 2200 is shown in FIG. 22. In this example, raw materials 2202 may include unconjugated lgG, lgA, and BSA, lgM preconjugated with dye, Alexa Fluor labelling kits, SARS-COV-2 S1 protein, epoxy silica magnetic beads, etc. Protein labeling 2204 may include labeling lgG Antibody with Alexa Fluor Dye A, labeling lgA Antibody with Alexa Fluor Dye B, labeling BSA with Alexa Fluor Dye C, etc. Bead preparation 2204 may include affixing BSA labelled with Alexa Fluor C to epoxy silica magnetic beads, affixing S1 protein to epoxy silica magnetic beads, etc. Mixing 2206 may include mixing lgG labelled with Alexa Fluor A, Labelled lgM, lgA labelled with Alexa Fluor B, etc. to form Labeled Antibody Solution 2208, and mixing BSA beads, S1 beads, etc., to form bead solution 2210.

Figure 25:
FIG. 25 is an exemplary illustration of an analyzer device according to embodiments of the present techniques.
Figure 26:
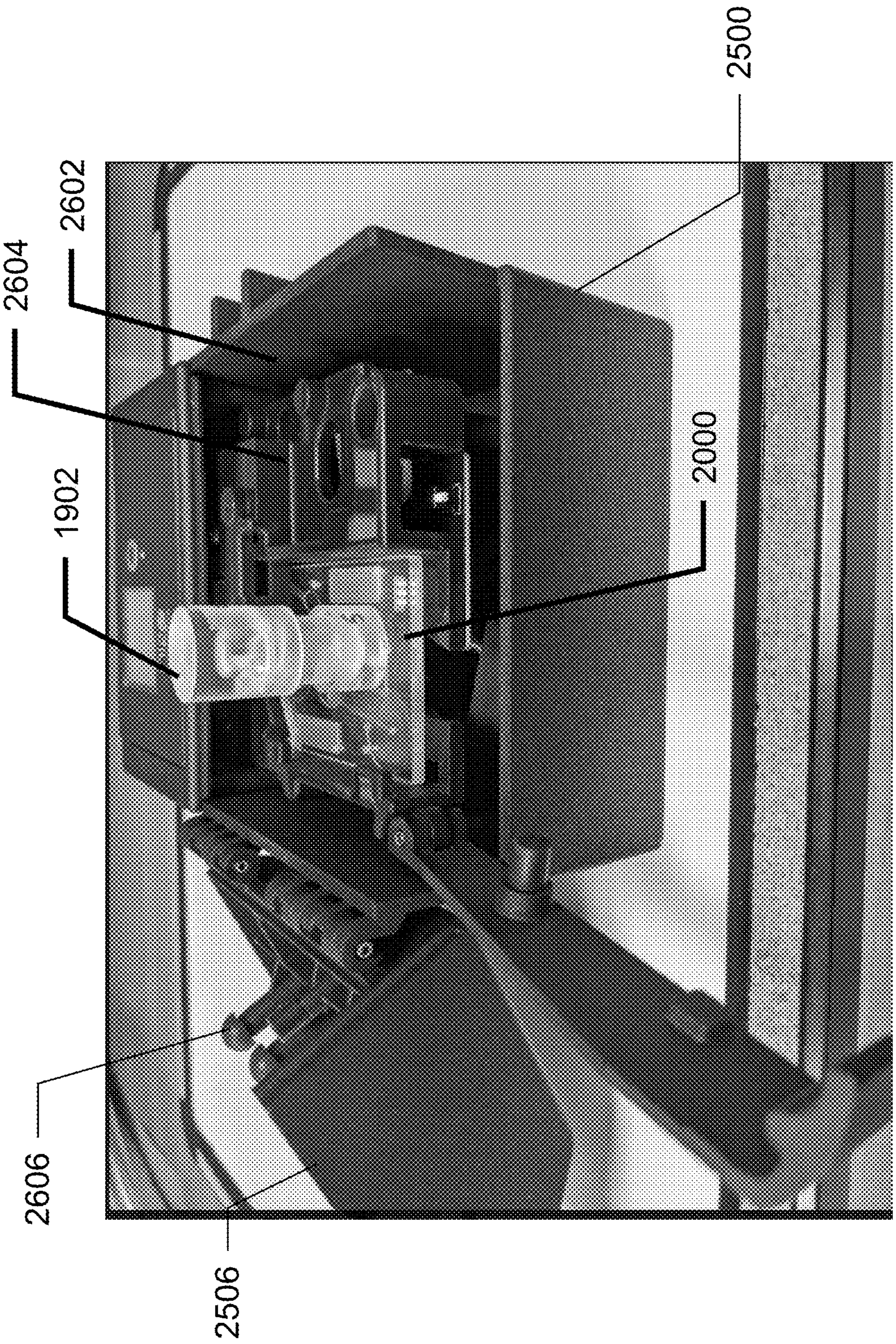
FIG. 26 is an exemplary illustration of an analyzer device according to embodiments of the present techniques.
Figure 27:
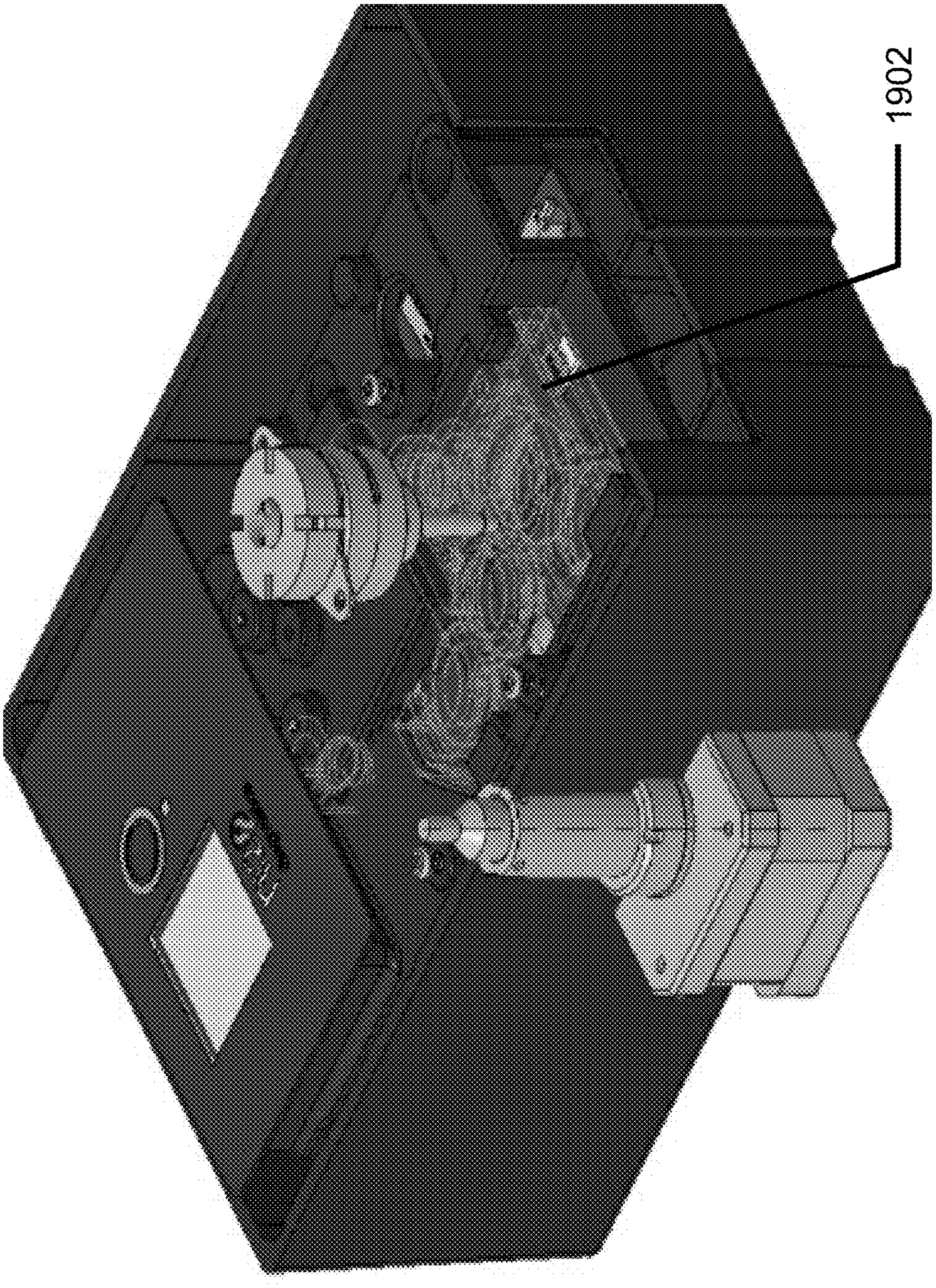
FIG. 27 is an exemplary illustration of an analyzer device according to embodiments of the present techniques.

An exemplary embodiment of an analyzer device 2500 is shown in FIGS. 25, 26, and 27. Analyzer device 2500 may, for example, be assembled using a combination of 3D-printed and/or injection molded plastic materials, glass, mirror, microprocessors, and various electronic components.

This low cost, portable device accepts the disposable cartridge 2000, performs the automated assay, and displays the results on an integrated display 2502, such as an LCD screen. Test results can also be output using the built-in USB-C port 2504 and on-board firmware which allows for interfacing with a laptop computer or a mobile device. The device uses a latchable door 2506 which holds the cartridge in place during the test, blocks ambient light from entering the detector area, and provides the actuation force to dispense the blisters. When the door is closed, the wash reservoirs fill, and the device performs automated test functions. Actuation of a permanent magnet within the device moves the magnetic particles; implementing mixing and washing actions, as well as transferring the particles between chambers and positioning them in the detection area. The device then performs the automated fluorescence detection process and outputs the results.

FIG. 26 further shows a loading bay or area 2602 for receiving a cartridge 2000. Loading bay or area 2602 may include a bracket to hold cartridge 2000 during testing. Also shown is latchable door 2506 with the plurality of prongs that provide the actuation force to dispense the blisters.

In embodiments, the analyzer device 2500 may be a low cost, reusable unit that accepts the disposable cartridge 2000, performs the automated assay, and displays the results on an integrated display 2502, such as a black and white LCD. The device may operate on an internal 5V power supply which may be plugged into a wall outlet. A latching door on top of the unit may provide three functions: it may hold the cartridge in place during the test, it may block ambient light from entering the detector area, and it may provide the actuation force to dispense the blisters at the beginning of the assay. A permanent magnet 808, shown in FIG. 8, may be moved under the cartridge with a linear actuator 804 to move the magnetic particles, implementing mixing and washing actions as well as moving the particles between chambers and positioning them in the detection area. An array of three LEDs may provide excitation light at frequencies specific to the label dyes in the cartridge. Optical short-pass filters may further tune the wavelength cutoff characteristics of the LEDs to improve detector sensitivity. A pair of six-channel optical sensors may be used to detect twelve different emission wavelengths. The LED array and optical sensors may be positioned 90 degrees from each other to minimize detection of the excitation sources, improving sensitivity. LED intensity and sequencing, detector gain and integration time, actuator parameters such as chamber location, speed, and mixing time, and detection thresholds may be adjusted automatically by the device based on the requirements of the assay. These parameters may be selected during the test by identifying the cartridge type via an authentication integrated circuit 718, shown in FIG. 7, embedded in the cartridge.

In embodiments, the analyzer device 2500 may include a built-in USB-C or other port, and or wireless communications connectivity, such as Bluetooth, WiFi, etc., and on-board firmware that allows for interfacing with, for example, a laptop computer or a mobile device. Through this interface, it may be possible to perform additional functions via connected applications. In its simplest form, an application may store the results of the tests and provide the patient with access to their test results after leaving the test site. The fully integrated system may assist infectious disease surveillance via connections to public health action initiatives and large-scale disease data collection. Analyzer device 2500 may also interface with other software for contact tracing and real-time data collection. Disease surveillance facilitation could help the NIH and CDC track and predict outbreaks as well as support their decision-making process during pandemic emergencies. A connected app could be individualized to give tailored, user-specific predictions of disease progression, contagiousness, quarantine, and suggestions or recommendations on resources for treatment. Embodiments may include hybrid tools that combine surveillance with large-scale data analysis for development of more accurate disease modeling and forecasting.

Figure 28:
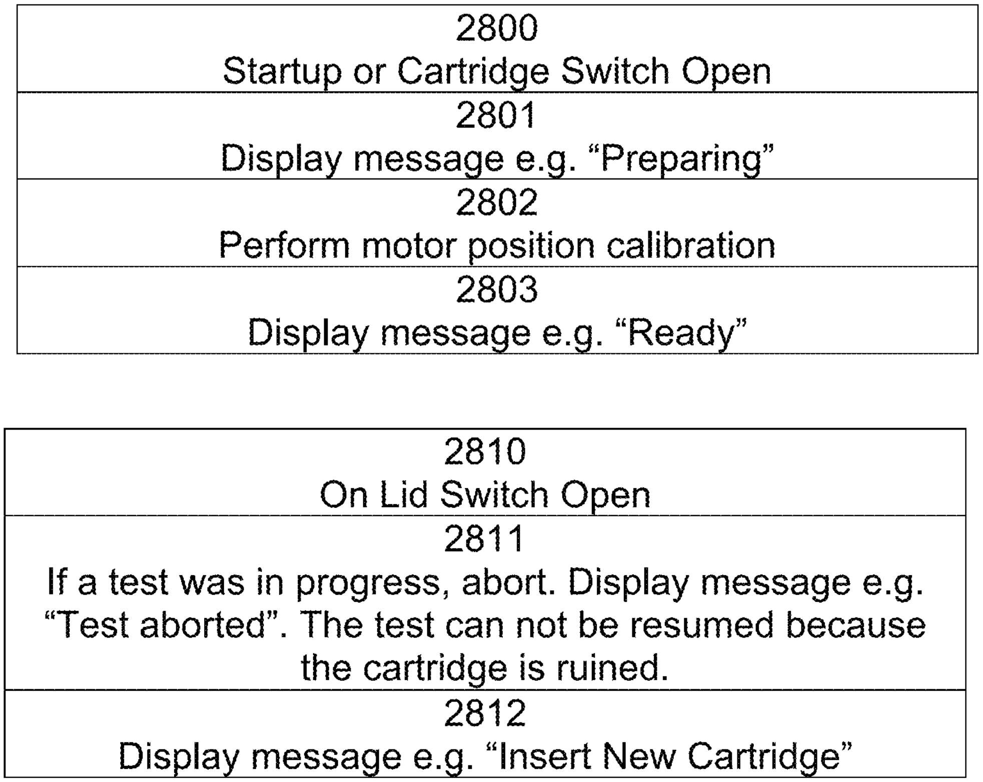
FIG. 28 shows exemplary flow diagrams of processes of operation of an analyzer device according to embodiments of the present techniques.

Processes of operation of analyzer device 2500 are shown in FIGS. 28, 29, and 30*a-c*. For example, a process of Startup or Cartridge Switch Open 2800 is shown in FIG. 28. Upon Startup or Cartridge Switch Open 2800, device 2500 may display a message, such as "Preparing" 2801, perform motor position calibration 2802, and display message, such as. "Ready" 2803. A process of Lid Switch Open 2810 is also shown in FIG. 28. When the Lid Switch Open 2810 occurs, at 2811, if a test was in progress, the test is aborted. Device 2500 may display a message, such as "Test aborted". The test cannot be resumed because the cartridge is ruined. If there was no test in progress, then at 2812, device 2500 may display a message, such as "Insert New Cartridge".

A process of On Cartridge Switch Close 2900 is shown in FIG. 29. When Cartridge Switch Close 2900 occurs upon insertion of a cartridge, at 2901, the authentication chip may be read and the cartridge parameters obtained. At 2902, if the cartridge parameters indicate that the cartridge is already used and that cartridge parameters contain test results, then at 2902*a*, device 2500 may display those test results, and may display an indication that the results are for a previously performed test. If the cartridge parameters do not contain test results, then device 2500 may display a message such as "Cartridge Prev. Used". If the cartridge is not previously used, then at 2903, the magnet 808, shown in FIG. 8, may be moved to pneumatic port sealing location to ready it to operate during the test. At 2904, device 2500 may configure the test using parameters included in the cartridge parameters. At 2905, device 2500 may display a message, such as "Close Lid".

A process of On Lid Switch Close is shown in FIGS. 30*a-c*. When Lid Switch Close 3001 occurs upon closing of the lid of device 2500, at 3001, device 2500 may display a message such as "Analyzing" and may further display a countdown timer indicating a time until completion of the test. At 3002, the cartridge may be marked as used in the cartridge authentication chip memory. At 3003, device 2500 may wait a short time for depression of the blisters 2008, 2010, 2012, shown in FIG. 20. Waiting too long may pull down too many beads, but we do need to wait for dispensing to be complete. In embodiments, this wait time may be configured using parameters included in the cartridge parameters.

At 3004, the magnet may be moved quickly away, possibly all the way to the detection area, but at least past the first mixing chamber. The magnet may be moved fast enough to not drag beads. At 3005 the magnet may be moved slowly back to the sample area 1902, shown in FIG. 19, possibly oscillating to catch straggler beads. At 3006, the magnet may be moved quickly away again, just to the first mixing area 2002, shown in FIG. 20, for example.

At 3007, an LED calibration run may be performed. a. Using the lime LED, which emits into a spectrometer channel that we can read, perform a series of measurements to characterize the LED intensity drift over the sampling period. At 3007*a*, using the lime LED, which emits into a spectrometer channel that can be read, a series of measurements to characterize the LED intensity drift over the sampling period may be performed, for example, as follows. At 3007*a.i*, an LED of a selected color, such as lime, may be turned on to a level near full brightness, for example, 80%. At 3007*a.ii*, device 2500 may wait 1 integration time (for example, 180 ms) for any erroneous initial reading to clear. In embodiments, this integration time may be configured based on parameters of device 2500 and/or based on parameters included in the cartridge parameters. At 3007*a.iii*, device 2500 may read, for example, 6 samples of channel R (610 nm) at that integration time (for example, total elapsed sampling time=6*2*180 ms=2.16 s). At 3007*a.iv*, device 2500 may calculate a linear fit for the LED PWM that would generate a flat spectrometer reading of a certain amplitude over those points. At 3007*a.v*, this same calculation may be applied to the other two LEDs, which, in embodiments, may not be read directly with the spectrometer.

At 3008, when the incubation time has nearly passed, the magnet may be moved back under the sample area to pull down remaining beads that haven't already precipitated. In embodiments, the incubation time, magnet movement time, remaining precipitation time, etc., may be configured based on parameters of device 2500 and/or based on parameters included in the cartridge parameters.

At 3009, a baseline fluorescence measurement may be performed as follows. At 3009*a*, a baseline fluorescence measurement may be performed using the illumination intensity curve from the LED calibration run 3007 for each of the three LEDs. At 3009*b*, for, for example, IgM: Channel G/560 nm, Blue LED, at 3009*b.i*, the LED may be turned on using the calibration curve from 3007. At 3009*b.ii*, device 2500 may wait 1 integration time (for example, 180 ms) for any erroneous initial reading to clear. At 3009*b.iii*, device 2500 may read 6 samples of spectrometer channel at that integration time. At, 3009*c*, for, for example, IgG: ChannelR/610 nm, Lime LED, at 3009*c.i* the LED may be turned on using the calibration curve from 3007. At 3009*c.ii*, device 2500 may wait 1 integration time (for example, 180 ms) for any erroneous initial reading to clear. At 3009*c.iii*, device 2500 may read 6 samples of spectrometer channel at that integration time. At 3009*d*, for, for example, IgA: Channel J/705 nm, Deep Red LED & Internal Standard: Channel U/760 nm, Deep Red LED, at 3009*d.i* the LED may be turned on using the calibration curve from 3007. At 3009*d.ii*, device 2500 may wait 1 integration time (for example, 180 ms) for any erroneous initial reading to clear. At 3009*d.iii*, device 2500 may read 6 samples of spectrometer channel at that integration time.

At 3010, device 2500 may perform bubble detection by looking for abnormally high spectrometer readings. At 3011, device 2500 may move the bead mass to the first (mixing) chamber 2002. Oscillating motion may be required to keep mass from breaking up. At 3012, device 2500 may agitate by moving magnet 808 for the second incubation time, such as 120 seconds. In embodiments, the incubation time, etc., may be configured based on parameters of device 2500 and/or based on parameters included in the cartridge parameters. At 3013, device 2500 may move the bead mass to the second (washing) chamber 2004, shown in FIG. 20, by moving magnet 808. Oscillating motion may be required to keep mass from breaking up. At 3014, device 2500 may agitate for the washing time, such as 30 seconds, by moving magnet 808. In embodiments, the incubation time, etc., may be configured based on parameters of device 2500 and/or based on parameters included in the cartridge parameters. At 3015, device 2500 may move the bead mass to the detection area by moving magnet 808. Oscillating motion may be required to keep the mass from breaking up. At 3016, device 2500 may perform a fluorescence measurement using a procedure similar to that at 3009. At 3017, device 2500 may calculate the relative signal between the fluorescence and baseline measurements, for example, by subtracting the baseline measurements from the fluorescence measurements. At 3018, device 2500 may calculate the three ratiometric signals by scaling to the internal standard measurement. At 3019, device 2500 may map the three ratiometric signals to antibody or other readings. At 3020, device 2500 may display the results.

Figure 31:
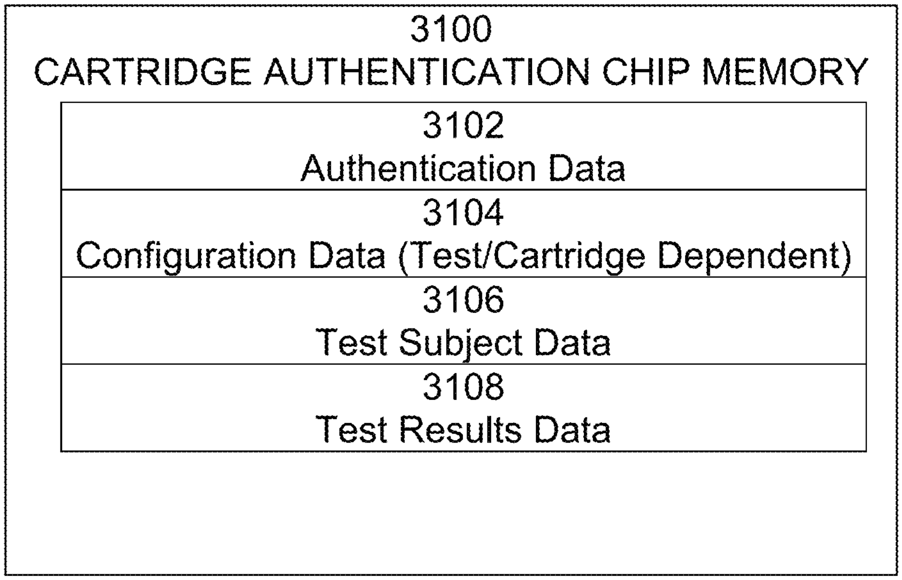
FIG. 31 is exemplary format of a memory of a cartridge authentication chip according to embodiments of the present techniques.

An exemplary format of memory of a cartridge authentication chip 3100 is shown in FIG. 31. In this example, cartridge authentication chip memory 3100 may include authentication data 3102, configuration data 3104, test subject data 3106, and test results data 3108. Authentication data 3102 may include data that may be used to authenticate the cartridge, data stored on the cartridge, etc. Configuration data 3104 may include data to identify the type of cartridge, the testing to be performed, configuration data for initializing and performing the test, etc. Test subject data 3106 may include data relating to the person or animal being tested, for example, including identity, physical and medical information, etc. Test results data 3108 may include results data from a completed test or data indicated an aborted test.

The device and firmware architecture may allow for future expansion and upgrades, as well as adaptation to new versions of the single-use cartridge. The device may identify the type or version of the cartridge from the authentication chip. In embodiments, a connected application may also be used for updating the device firmware with support for additional types of cartridges, for example, adding new settings for magnet arm movement, LED brightness, optical sensor thresholds, and other parameters, etc. The versatility of the cartridges may provide expansion of this technology to screen for immunity towards other infectious diseases, such as seasonal influenza, as well as other conditions, whether infectious or not.

Embodiments may capture antibodies at a low limit of detection, while in embodiments, assay for viral antigen capture may be performed. This would involve substituting the immobilized capture protein with an immobilized antibody for a viral antigen on the magnetic beads. In addition, the labeled antibody that contains the fluorescent or enzymatic would be changed to a second antibody that binds to the virus and its viral antigen. The remaining components of the sandwich assay and the general assay format would be the same.

Embodiments may be extremely useful in emergency response and urgent care, informing doctors how to proceed with treatment without having to wait hours for a confirmatory test and informing decisions about whether or not to quarantine patients. Rapid determination of infectivity will also inform users of whether or not it is safe to return to school or work, gather in large groups, or travel. Moreover, individuals can feel confident that they will not bring the virus home to their families. These decisions, along with contact tracing methods, will allow us to track and slow the spread of pathogens.

Embodiments may provide sensitivity in the range of 95%. In embodiments, the assay may be optimized to have a linear response to the concentrations within the range of sensitivity. The assay may be reproducible within 5-10% and the instrument may self-calibrate down to the validated response range. Embodiments may provide specificity in the range of 97%. For example preliminary data suggest that SARS-CoV-2 antibodies bind to the S1 component of the virus, and that antibodies toward other viruses (such as RSV and MERS) show no statistically observable response vs a blank standard with no antibodies present for SARS-CoV-2. The dynamic range of the device may be set using a signal-to-noise ratio of at least 10 for quantitation or using a value of 3 for a qualitative screening assay. Embodiments may provide an analytical limit of detection when using direct fluorescence detection and 100-200 μL of saliva of <1 nM (~0.5-0.7 nM). Embodiments may provide a precision of ±5-8% over most of the calibration range. In terms of robustness, embodiments may provide less than 5% of variability between test cartridges. In terms of accuracy, embodiments may be no less than 95% accurate with a false positive and false negative output of no more than 5%. Embodiments may perform each test in less than 5 minutes, with a throughput of 12 tests per hour.

Embodiments may use beads containing human lgM, human lgG or human lgA (Int. Std., Alexa-568 BSA beads; 5 min incubation) may be placed into pH 7.4, 0.067 M phosphate buffer containing 0.1% sodium azide, for use transport and long-term storage at 4° C. The immunoglobulin-containing beads were found to still show a good response in a sandwich assay when stored under these conditions. These data are consistent with previous results indicating that sodium azide did not have any significant effect on the response for this type of sandwich assay.

Embodiments may use beads containing the new spike protein S1 beads (ACRO Biosystems) (Int. Std., Alexa 568 BSA beads; 2.5 min+2.5 min split incubation) were also placed into pH 7.4, 0.067 M phosphate buffer containing 0.1% sodium azide, for use transport and long-term storage at 4° C. The spike protein S1 beads were also found to show a good response in a COVID antibody sandwich assay when stored under these conditions. These data were again consistent with previous results indicating that around 0.1% sodium azide did not have any significant effect on the response for this assay.

Embodiments may use Alexa Fluor 750 BSA beads (using human lgM beads, FITC-labeled anti-human lgM antibodies and new Alexa-750 BSA beads as the internal standard (5 min incubation)) were prepared for use as an internal standard in a COVID-19 antibody assay with multi-channel detection. These beads gave a response and protein content that was consistent with previous batches of the same material. These beads were also examined for their response in a sandwich assay (demo format 1) after they were transferred to a pH 7.4 buffer containing 0.1% sodium azide for long term storage. A good response and low background signal was again seen when these beads were used in these assays.

Embodiments may use beads that contain immobilized lgG, lgA or lgM, combined with a mixture of secondary labeled antibodies, models binding of labeled antibodies with adsorbed targets on beads. Example may include FITC rabbit anti-human lgM (mu chain specific), Alexa 680 anti-human lgA (alpha chain specific, prescreened vs lgG & lgM), Alexa 568 anti-human lgG (H+L chains) (commercial), Alexa 568 anti-human lgG (Fe specific chains), Alexa Flour 488 goat anti-human lgM (mu chain specific), etc.

Embodiments may use sandwich immunoassay that can be used to detect SARS-CoV-2 antibodies in biological samples and can detect multiple antibodies simultaneously in a tube-based assay. Embodiments may be easily repurposed for use with a viral detection assay.

Embodiments may include the capture component of the assay with a model assay using Human Serum Albumin (HSA). Incubation of diluted anti-HSA rabbit antiserum with fluorescein-labeled anti-rabbit IgG antibodies, and injection of 20 μL mixture at 1.0 mL/min onto 2.1 mm I.D.×5 mm HSA column may yield a column residence time of 0.5 seconds. This may indicate that the capture component can take less than a few minutes. This result has been verified in work with the magnetic beads. The estimated detection limit in work with the model system and the beads in a solution phase assay is currently 0.3 nM at a signal to noise ratio of 3 for the target.

Embodiments may be used without enzymatic amplification to detect SARS-CoV-2 antibodies at nanomolar concentrations. Beads containing approximately 10 mg fluorescent-labeled proteins per gram of beads may be easily be detected at final bead levels down to less than 0.01 mg/mL. The use of enzymatic amplification with horseradish peroxidase (HRP) may allow detection limits down into the picomolar range. HRP-labeled antibodies are detected down to 65-70 pM in 2.5 to 5 min. This detection limit is well below that needed to detect typical antibody levels in saliva (0.3-0.4 nM). The relative amount and type of secondary antibodies, fluorescent label, capture agents, and volume of sample may be modified to obtain lower limits of detection.

In embodiments, the final number of beads needed for detection are between 0.1-0.05 mg/mL in 20 μL. The content of capture protein on the beads are between 5 to 10 mg/g beads. Labeled secondary antibodies may be used in excess, >2× the concentration of target antibodies. This assay gives a linear response with a mass-mol detection limit that is well below that needed with small samples of whole saliva (100-200 μL).

Typically, the beads do not have a significant background fluorescence which might interfere with the assay also do not have significant non-specific binding to components of the sample and reagents for the assay. Multiple dye labels, such as FITC, Alexa Fluor 488, Alexa Fluor 568, Alexa Fluor 680, and Alexa Fluor 750 may be used with this assay format in the simultaneous detection of multiple analytes (e.g., multiple antibodies or viral strains plus a positive control) in a microchip-based device.

Good stability was seen for capture protein beads over at least 3 months of use, as well as good reproducibility in protein content and assay behavior over multiple batches of beads. Over the course of five days, the presence of BSA does not appear to contribute to bead aggregation during storage at 4° C.

Various pH 7.4 buffers may be used. Several types of buffers, such as potassium phosphate, or phosphate buffered saline, may be acceptable for use with the assay. In embodiments, rabbit IgG anti-spike protein antibodies may be used with either buffer (both with Tween 20 as an additive) in the sandwich assay for COVID spike protein antibodies. Embodiments may use up to 2.5 mM sodium azide as a preservative in the assay an may provide an acceptable assay response.

In embodiments, lowering the amount of assay beads on the response may cause some decrease in assay range, but a usable response may be obtained for a 2- or 4-fold decrease in assay bead levels. In terms of selectivity, the assay components may give no significant response to non-specific/generic antibodies (e.g., samples of human IgG) or the matrix components of normal pooled human saliva. Embodiments may have highly specific selection for SARS-CoV-2 antibodies compared to antibodies toward other viruses, such as SARS, MERS, RSV, HCV, and autoimmune antinuclear antibodies. No statistically observable response is seen with antibodies toward other viruses or toward ANA vs a blank standard with no antibodies present for SARS-CoV-2.

The ability to carry out multianalyte detection was confirmed and tested in a four-channel method by using 1) mixtures of labeled beads, 2) mixtures of labeled antibodies with immunoglobulin beads, and 3) various types of spike protein antibodies in a sandwich assay. We have successfully demonstrated the simultaneous detection of four analytes, IgA, IgM, IgG, and an internal standard, with cross-reactivity between the 3 antibodies or the internal standard, demonstrating high interclass specificity. Using a split incubation format (2.5 min in tube incubation and 2.5 min run time) gave the best improvement in assay response. Detection in the low nM range was seen, as noted previously, along with little or no hook effect at higher levels over the range of tested concentrations. Further analysis was also carried out on detection of these labels by a microchip-based detector in either the sample holder used originally vs a prototype cartridge, giving comparable trends in detection. The assay can be used with either a specific response at a given channel or with multiplexing for signals with a mixed response.

In embodiments, a sample collection kit may include on-board foil-sealed liquid reagents, including the functionalized magnetic beads and secondary antibodies needed for the detection assay. The kit also includes an attachable funnel to facilitate easy collection of the saliva sample, and a foil piercing system to interface with the cartridge. After providing the saliva sample, the user shakes the collection kit for 30 s to mix the pre-stored liquid reagents and saliva sample prior to insertion into the cartridge.

The compatible cartridge, with dimensions of, for example, 75 mm (L)×50 mm (W)×10 mm (H), may include a smart laminate, an injection molded part with blister piercing features, three blisters, and an injection molded case. The cartridge may be equipped with an inlet port for attachment of the sample collection kit, two 250 μl buffer solution blisters with adjacent 22 μL wash chambers, one air-filled blister for pneumatic control, a detection window, overflow passages, fluidic paths, and a valve to ensure proper fluid routing. The blisters of the cartridge are actuated by the closing of the top lid of the device.

Examples of pathogens or antibodies to pathogens that may be detected based on target substances may include West Nile virus, Malaria, Zika, Ebola, Tuberculosis, Hepatitis A, Hepatitis B, Hepatitis C, HIV/AIDS, Influenza A/B, etc. Example of other conditions that may be detected based on target substances may include Diabetes, Enzyme Markers, such as for CPK-1--+Brain injury after concussion, CPK-2, CPK-3, and Troponin, conditions that may be detected by a Coagulation Panel, such as hemophilia, acute myeloid leukemia, thrombosis, vitamin K deficiency, Prothrombin time (PT), Fibrinogen activity test, C-reactive Protein Test-inflammation, conditions that may be detected by a Cholesterol lipid panel including LDL level, HDL level, triglyceride level, conditions that may be detected by a Thyroid Panel including T3, T4, RU, TSH, Alzheimer's disease or other diseases based on, for example, Amyloid Beta Peptide, Tau protein, Lactoferrin, Alpha synuclein, DJ-1 Protein, Chromogranin A, and Huntingtin protein, Cognitive Decline based on, for example, Glucocorticoids, Cortisol, conditions such as Coeliac disease, Stomach Cancer, Breast Cancer based on, for example, CA 15-3 antigen for breast cancer, SPM, CAD, Ac-SPM, N1-Ac-SPD, N8-Ac-SPD polyamines in saliva, Prostate Cancer based on prostate-specific antigen (PSA), Colorectal cancer based on Carcino-EmbryonicAntigen (CEA), Gastrointestinal Cancer based on CA 19-9 antigen, Ovarian Cancer based on CA 125 antigen, etc. For example, types of cancer that may be detected based on known markers may include breast, prostate, gastrointestinal, ovarian, and colorectal cancers. Hepatitis A and B may be detected based on known markers. Thyroid disorders may be detected based on known markers such as T3, T4, RU, TSH, etc. Cholesterol issues may be detected based on known markers such as LDL, HDL, triglycerides, etc. Alzheimer's may be detected based on known markers such as Tau protein, Amyloid Beta, Peptide, Alpha synuclein, DJ-1 Protein, Chromogranin A, etc.

Embodiments may include analyzer devices which automate the assay using low cost, readily available components. Embodiments may control magnetic particles in a microfluidic cartridge using a permanent magnet on a linear actuator, for moving the particles between chambers on the cartridge as well as performing mixing and washing actions. Embodiments may perform fluorescent dye excitation and detection using cost-effective LEDs and multi-channel light sensors, and fluorescence detection from dye-labeled magnetic particles in concentrations representative of those present in the assay. Embodiments may include positioning and sequencing three light sources, combined with optical short-pass filters to excite fluorescence in four separate dyes, detecting a positive control and up to three separate analytes in a single sample. The adjustability of components in this system, as well as the ability to detect multiple analytes, allows for significant flexibility and expansion of assay development and testing.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A system comprising:

a cartridge comprising:

a first chamber configured to receive a test sample including a target substance, the first chamber filled and hermetically sealed during manufacture of the cartridge with micromagnetic particles treated so as to bind to the target substance;

a first reservoir filled and hermetically sealed during manufacture of the cartridge with at least one reagent labeled with at least one fluorescent compound, the reagent adapted to bind to micromagnetic particles that are bound to the target substance; and an authentication chip adapted to provide authentication of the cartridge, identification of the cartridge, and data storage for the cartridge including providing test configuration parameters for initializing and performing the test, test subject data relating to a person or animal being tested, and storing test results data comprising results data from a completed test or data indicating an aborted test; and an apparatus comprising:

a light source disposed so as to excite the at least one fluorescent compound with a light;

an optical sensor disposed so as to detect an emitted spectrum of light from the excited at least one fluorescent compound;

a loading bay disposed on the apparatus to receive the cartridge; a door disposed on the apparatus to cover the loading bay;

at least one blunt prong disposed on an interior of the door to provide actuation force directly from the at least one blunt prong to at least one blister reservoir disposed on the cartridge when the door is closed, so as to dispense the at least one blister reservoir; and a device disposed relative to the cartridge to move at least a portion of contents of the cartridge among a plurality of chambers of the cartridge;

wherein the device disposed relative to the cartridge to move at least a portion of the contents of the cartridge among chambers of the cartridge comprises a motor having disposed on a drive shaft thereof a pinion, a rack meshed with the pinion, and a magnet disposed on the pinion and disposed relative to the cartridge so as to move at least a portion of the contents of the cartridge among chambers of the cartridge when the motor is driven;

wherein driving of the motor is controlled by a computer system comprising a processor, memory to store program instructions and data and accessible by the processor, and program instructions stored in the memory and executable by the processor to control driving of the motor; and wherein the apparatus is configured to read data from the authentication chip upon insertion of the cartridge into the apparatus.

2. The system of claim 1, wherein the light source comprises at least one excitation light emitting diode disposed so as to excite fluorescence of the at least one fluorescent compound.

3. The system of claim 2, wherein the optical sensor comprises at least one photodiode disposed so as to detect the excited fluorescence of the at least one fluorescent compound and to output a signal representing the detected fluorescence.

4. The system of claim 1, wherein the first reservoir is filled and hermetically sealed during manufacture of the cartridge with a plurality of reagents each labeled with a different one of a plurality of fluorescent compounds.

5. The system of claim 4, wherein the light source comprises a plurality of excitation light emitting diodes disposed so as to excite fluorescence of the plurality of fluorescent compounds.

6. The system of claim 5, wherein the optical sensor comprises at least one photodiode disposed so as to detect the excited fluorescence of the plurality of fluorescent compounds and to output signals representing the detected fluorescences.

7. The system of claim 6, wherein each of the plurality of fluorescent compounds has a wavelength range that does not overlap with at least some of the others of the plurality of fluorescent compounds.

8. The system of claim 1, wherein at least the first reservoir is a blister reservoir.

* * * * *